US009717841B2

(12) United States Patent
McNeil

(10) Patent No.: US 9,717,841 B2
(45) Date of Patent: Aug. 1, 2017

(54) CLOSED-CIRCUIT DEVICE AND METHODS FOR ISOLATION, MODIFICATION, AND RE-ADMINISTRATION OF SPECIFIC CONSTITUENTS FROM A BIOLOGICAL FLUID SOURCE

(71) Applicant: Gary L. McNeil, Marlborough, MA (US)

(72) Inventor: Gary L. McNeil, Marlborough, MA (US)

(*) Notice: Subject to any disclaimer, the term of this patent is extended or adjusted under 35 U.S.C. 154(b) by 581 days.

(21) Appl. No.: 13/843,778

(22) Filed: Mar. 15, 2013

(65) Prior Publication Data

US 2014/0074007 A1    Mar. 13, 2014

Related U.S. Application Data

(60) Provisional application No. 61/699,433, filed on Sep. 11, 2012.

(51) Int. Cl.
*A61M 1/36* (2006.01)
*A61M 1/34* (2006.01)
(Continued)

(52) U.S. Cl.
CPC .......... *A61M 1/367* (2013.01); *A61M 1/3486* (2014.02); *A61M 1/362* (2014.02);
(Continued)

(58) Field of Classification Search
CPC ........ A61M 1/34; A61M 1/3472; A61M 1/75; A61M 1/79; A61M 1/82; A61M 1/86
See application file for complete search history.

(56) References Cited

U.S. PATENT DOCUMENTS 4,430,229 A    2/1984 Yamawaki et al.
4,685,900 A    8/1987 Honard et al.
(Continued)

FOREIGN PATENT DOCUMENTS

WO    WO 2006/017763    2/2006

OTHER PUBLICATIONS

Pietersz et al., "The use of monoclonal antibody conjugates for the diagnosis and treatment of cancer", Immunol. Cell Biol., 65: 111-125 (1987).

*Primary Examiner* — Leslie Deak
*Assistant Examiner* — Kai Weng
(74) *Attorney, Agent, or Firm* — Leon R. Yankwich; David G. O'Brien; Yankwich & Associates, P.C.

(57) ABSTRACT

The present invention relates to a method and apparatus for the isolation, modification and re-administration of a molecule or biomolecule, or a class of biomolecules, from the body fluid of a mammal via an extracorporeal closed circuit device. The device is able to capture and modify the biomolecule by the covalent or non-covalent attachment of a secondary molecule or protein, by cross-linking the captured molecule, or by altering the structure of the molecule (for example, by deglycosylation, peptide cleavage, or aggregation). The apparatus can be used to return the modified molecule or biomolecule to the mammalian subject. The device and methods may be utilized for the patient-specific diagnosis and/or treatment of a disease state which presents an associated molecule or protein in plasma or any other fluidized physiological system.

The methods and apparatus may also be employed as a closed system allowing the on-line purification and/or modification of a target molecule or biomolecule from a fluid source such as a bioreactor or perfusion bioreactor.

30 Claims, 4 Drawing Sheets

(51) Int. Cl.
*G01N 33/564* (2006.01)
*B01J 20/32* (2006.01)
*A61B 5/15* (2006.01)
*A61B 6/03* (2006.01)

(52) U.S. Cl.
CPC ....... *B01J 20/3204* (2013.01); *B01J 20/3212* (2013.01); *B01J 20/3274* (2013.01); *G01N 33/564* (2013.01); *A61B 5/15003* (2013.01); *A61B 5/150221* (2013.01); *A61B 5/150755* (2013.01); *A61B 5/150992* (2013.01); *A61B 6/037* (2013.01)

(56) References Cited

U.S. PATENT DOCUMENTS

| | | |
|---|---|---|
| 5,780,033 A | 7/1998 | Torchilin et al. |
| 6,039,946 A | 3/2000 | Strahilevitz |
| 6,497,675 B1 | 12/2002 | Davankov |
| 6,866,846 B1 | 3/2005 | Heinrich et al. |
| 7,799,327 B2 | 9/2010 | Smith et al. |
| 2005/0003484 A1* | 1/2005 | Hirano ............. C07K 14/70539 435/69.1 |
| 2005/0006296 A1* | 1/2005 | Sullivan et al. ........... 210/321.6 |
| 2007/0026029 A1 | 2/2007 | Mattner et al. |
| 2011/0004142 A1* | 1/2011 | Matson ........................ 604/6.09 |

* cited by examiner

CLOSED-CIRCUIT DEVICE AND METHODS FOR ISOLATION, MODIFICATION, AND RE-ADMINISTRATION OF SPECIFIC CONSTITUENTS FROM A BIOLOGICAL FLUID SOURCE

CROSS-REFERENCE TO RELATED APPLICATION

This application claims priority to U.S. Provisional Application No. 61/699,433, filed Sep. 11, 2012, the contents of which are incorporated by reference herein in their entirety.

FIELD OF THE INVENTION

The present invention relates to an apparatus and methods for the isolation, modification and re-administration of a biological target or targets, from a subject or patient via an extracorporeal circuit. The present invention alternatively relates to a diversion circuit from a bioreactor or conduit for media flow or circulation, which diversion circuit can be used to collect samples, alter biochemical elements in the circulating stream, and return modified elements to the bioreactor or the original conduit. The apparatus and methods are suitable for the evaluation, diagnosis, treatment and/or monitoring of a disease state in a subject or patient, or to test and monitor that state of biochemical elements in a bioreactor or conduit. The apparatus and methods are suitable for the purification of a biological target or targets from a fluid source while maintaining a closed system.

BACKGROUND OF THE INVENTION

Apheresis and hemodialysis methods are used to treat a variety of disease states which manifest themselves as a detrimental and potentially toxic increase of an innate or newly-presented component of the circulation system. Hemodialysis, for example, is used for treating patients suffering from renal failure; it involves the use of an artificial kidney to clear urea, metabolic waste products, toxins, and excess fluid from the blood before the blood is returned to the patient. Therapeutic apheresis is a procedure wherein whole blood is withdrawn from a patient, separated into two or more fractions, and at least one of the separated blood fractions is re-transfused into the patient, while the other fraction containing an unwanted or detrimental blood component is removed (discarded). The most common type of apheresis procedure is known as "plasmapheresis". In plasmapheresis, a quantity of liquid plasma is separated from a cell concentrate comprising the remaining liquid and cellular constituents of the blood and such cell concentrate is, thereafter, re-transfused into the donor. This process may remove whole cells or a specific population of cells. Other types of apheresis procedures include "leukapheresis" (wherein leukocytes are separated from whole blood) and "thrombocytapheresis" (wherein platelets are separated from whole blood). Apheresis procedures are also commonly carried out to harvest commercially usable blood components.

A number of devices and filter appliances directed at separation of various blood components have been developed and are commercially available for performing hemodialysis. For example, Fresenius Medical Care (Waltham, Mass.) manufactures a number of dialysis machines and membrane dialyzers (such as the Optiflux® Advanced Fresenius Polysulfone® and Hemoflow™ dialyzers) for separating waste components, such as urea, from a patient's blood using an extracorporeal circuit. Fresenius also manufactures and sells devices for therapeutic apheresis directed at removal of low density lipoprotein (LDL), e.g., to treat hypercholesteremia and for immunoadsorption, e.g., to remove autoantibodies from patients suffering from an autoimmune disorder (see, Prosorba®, Globaffin®, Immunosorba® dialysis products). These devices are used to substantially deplete the targeted molecules, for example immunoglobulins, from a patient's plasma using an extracorporeal circuit.

Apheresis devices reflect a variety of configurations and designs. U.S. Pat. No. 6,497,675 to Davankov describes an apheresis device for removal of low molecular weight toxins from a subject's blood by use of a hollow fiber membrane permitting passage of low molecular weight components of blood, which are then contacted with a particulate adsorbent material before remixing with the larger molecular weight components of the blood prior to return of the treated blood to the subject. U.S. Pat. No. 6,039,946 to Strahilevitz describes an extracorporeal affinity adsorption device for removing at least two chemical species from a body fluid of a patient. The system contains a complex circuit for on-line regeneration of a chelant. Such devices enhance the properties or cost-effectiveness of apheresis without altering the basic purpose of the apheresis techniques, which is the depletion or removal of a detrimental component from whole blood or other body fluid of a patient.

There has also been variegation of the targets addressed by apheresis devices as new classes of affinity materials have become available and new target molecules associated with disease states have been identified. For example, US Pat. Publication. 2007/0026029 (Mattner et al.) describes an apheresis device having a solid support containing a receptor for the capture of amyloid-β-precursor-protein from a subject's blood, for treating or preventing Alzheimer's disease. U.S. Pat. No. 4,430,229 (Yamawaki et al.) describes purine- or pyrimidine-based adsorbers for autoantibodies and immune complexes associated with collagen disorders such as systemic lupus erythematosus. WO 2006/017763 (Ellson and Mutz) describes removal of targeted biomolecules from a body fluid of a subject by contacting the fluid with a matrix of molecular imprint materials; U.S. Pat. No. 4,685,900 (Honard) describes removal of targeted biomolecules from a subject by contacting a body fluid with a specific biological ligand immobilized on a biocompatible polymer support (e.g., immobilized insulin molecules targeting anti-insulin autoantibodies in a diabetic); and U.S. Pat. No. 6,866,846 (Heinrich et al.) describes the preparation of patient-specific immunoadsorbers derived from immune complexes isolated from the patient.

All of the techniques/devices described above are designed for one primary purpose: to relieve or minimize the detrimental effect that a component of whole blood is exacting upon the patient by utilizing apheretic techniques to remove a significant proportion of the blood component permanently from the patient's circulation. In order to remove a physiologically beneficial amount of the component of interest, these techniques require the processing of large volumes of blood and the return of the depleted plasma to the patient. None of these methods or devices described above contemplate the isolation and modification of a targeted blood component, nor the return of the modified blood component to the patient, all within an extracorporeal closed-circuit apparatus.

SUMMARY OF THE INVENTION

In one aspect, the present invention is directed to a novel extracorporeal closed-circuit apparatus for withdrawing a body fluid from a mammalian subject, separating and immobilizing a target component of said body fluid, for example, a biomolecule, chemically or otherwise modifying the target component, and returning the modified component to the mammal. The body fluid can be blood, spinal fluid, amniotic fluid, cranial fluid, etc. The targeted component of the fluid may be any of a number of biomolecules present in the body fluid of a mammal that are capable of isolation and modification, i.e., proteins, nucleic acids, lipids, carbohydrates, etc.

In another aspect, the present invention is directed to a closed diversion circuit that can be connected to a fluid system, such as a bioreactor, for withdrawing a bioreactor fluid from the system, separating and immobilizing a target component of said fluid (for example, a biomolecule being produced in the bioreactor), chemically or otherwise modifying the target component, and returning the modified target component to the system. The fluid can be cell culture media, a chemical synthesis or biosynthesis feedstream, etc. The targeted component of the fluid may be any of a number of biomolecules that may be present in a fluid system and that are capable of isolation and modification, i.e., proteins, nucleic acids, lipids, carbohydrates, etc.

The apparatus of the present invention provides a closed, extracorporeal, optionally disposable, circuit for receiving the flow of body fluid from a subject, treating the fluid, and returning the fluid to the subject. The apparatus can be operated manually or by using automated machinery or control systems for pumping body fluid and other solutions through the apparatus. The apparatus described herein is suited for, but is not limited to, single use applications. The apparatus is designed to perform a series of functions, namely, receiving body fluid (such as whole blood or plasma) from an individual, separation of a target component from the body fluid, capture (immobilization) of a target component from the body fluid, such as IgG from whole blood, modification of the captured component by performing a chemical reaction or otherwise causing alteration of the captured component to produce a modified component, recombination of the modified component with untreated components of the body fluid, and return of the fluid containing the modified component to the individual, all in a closed circuit that avoids direct handling of any fluid components or exposure of the fluid to contaminants or the environment outside the circuit.

Separation of the target component from the whole body fluid is performed via a partitioning chamber, for example, when withdrawing blood, the partitioning chamber acts as a plasma separator for the separation of plasma containing the target component, e.g., antibodies, from the whole blood. Immobilization of the target component is via a sequestering chamber comprising a selective affinity matrix or capture support which functions to capture and immobilize the target component where it is held for the modification reaction preparatory to return of the targeted component by reinjection into the subject.

In one embodiment, the partitioning chamber (e.g., a dialyzer or other separator) allows the whole body fluid to be divided into a fraction containing the target component to be isolated and modified and a fraction that will not undergo any treatment and will continue circulating through the closed circuit of the apparatus and finally back to the subject from which the body fluid was initially taken. The membrane or membranes essentially divide the partitioning chamber into two sides, i.e., a retentate side on which non-targeted components of the body fluid are retained or prevented from passing through the membrane, and a filtrate side which contains the components that are allowed to penetrate through the membrane and which contains the targeted component, i.e., the component of the body fluid that includes the target molecule to be modified before return to the subject. This separation process may take place by osmosis. This separation process may be enhanced by utilizing differential pressure with either tangential filtration flow or separately in dead-end filtration mode.

The filtrate fraction of body fluid containing the target component that is separated from whole body fluid in the partitioning chamber is conducted to a sequestering chamber. The sequestering chamber of the apparatus is part of a closed system of compartments and valves located on the filtrate side of the partitioning chamber. The sequestering chamber includes a capture support (for example, a solid support with an immobilized selective adsorbent or affinity ligand, such as immobilized Protein A or Protein G for selectively capturing IgG molecules) which will bind or sequester targeted component (for example, immunoglobulins when Protein A or Protein G is the adsorbent) from the separated fraction of body fluid received from the partitioning chamber. When the filtrate fraction is contacted with the capture support of the sequestering chamber, at least a portion of the target component in the filtrate is bound and immobilized by the affinity ligand or capture adsorbent of the capture support. The capture support having the target component captured thereon can then optionally be flushed with various solutions, e.g., reactants, wash buffer, etc., which can be separately compartmentalized within the apparatus and introduced into the sequestering chamber at the direction of the person or system operating the apparatus, to prepare the captured target molecules for and then subject the target molecules to a reaction or alteration procedure. For example, target immunoglobulins separated from plasma from a patient may be sequestered and immobilized on a Protein A or Protein G adsorbent within the sequestering chamber, then further solutions may be introduced to wash the immobilized immunoglobulins, reagent solutions containing a desired reactant such as a radiolabeled linker may be introduced to chemically react with the target immunoglobulins, and further eluant solutions may be subsequently introduced to dissociate the modified (e.g., radiolabeled) immunoglobulins from the adsorbent. Alternatively, targeted molecules may be bound, washed, and then eluted into a separate compartment where labeling or modification takes place. The modified target may then be bound, washed and eluted again in order to remove byproducts of the modification process.

The modified target components eluted from the capture support are reintroduced to the retentate side of the partitioning chamber for remixing with retentate components of the body fluid and ultimately reintroduction of the body fluid, now containing modified target molecules into the subject from which the body fluid was removed. The reintroduction of modified target component may advantageously be carried out by conducting the eluate from the sequestering chamber into a collection compartment for remixing with the retentate or, as necessary, for further reaction steps (e.g., dilution, neutralization, warming) to make the modified target component suitable for co-mingling with returning body fluid being directed back into the subject.

The isolated target components can be chemically or physically modified, labeled with a detectable moiety, or conjugated with a therapeutic moiety. Labels and therapeutics moieties may be bound covalently or non-covalently to the target components. In one embodiment, the isolated molecules are reintroduced to the partitioning chamber by osmotic transport or differential pressure across the same sterile membrane located within the partitioning chamber, where they remix with the retentate fraction of the body fluid in the partitioning chamber and are thereafter reinjected into the patient. In a further embodiment, one or more sampling ports are provided in the circuit by which samples of the filtrate, purified target molecules, modified target molecules, and/or remixed, treated body fluid, can also be isolated for use in diagnostic assays or other tests. If such sampling ports are constructed so as to preserve the closed circuit, e.g., by sampling via sterile needle through an airtight, fluid impermeable septum, then samples can be removed from the apparatus during operation for testing and analysis. It is also contemplated that sampling circuits can be created within the apparatus, so that the samples are not removed from the closed circuit, even though they may be permanently isolated from the flow of the body fluid through the device. These sampling circuits may contain multiple compartments connected in series or in parallel. Filters or various binding supports may be positioned between these compartments in order to remove an unwanted component, or to bind and retain a component of interest. These sampling circuits may be removed from the apparatus either during or following the procedure without compromising the closed system.

In yet another aspect of the present invention, a method for treating a body fluid component is provided which accomplishes the treatment within a closed extracorporeal circuit, without exposure of the treated component to contaminants or the environment outside of the circuit. Such treatment methods are especially suitable for isolating and modifying a target component circulating in an individual subject's blood. In a particular embodiment, the extracorporeal closed-circuit apparatus of the invention allows the capture and immobilization of a target molecule of interest from the plasma of a blood sample drawn from a subject, allows the modification of the isolated molecule to impart enhanced and/or novel physiological properties to the captured molecule, and then allows for return of the modified molecule to the subject for therapeutic or diagnostic purposes.

The modification of the target component can be any type of modification and for any purpose known in the art including conjugation with a detectable label, e.g., fluorescent, biotinylated, or radioactive labels; addition of functional groups or crosslinkers, e.g., thiols, carboxylates, amines, carbodiimides; chemical or structural modification such as deglycosylation, alteration of glycosylation, protein refolding, etc.; and covalent or non-covalent attachment of other molecules such as cytokines, cytotoxins, immunoglobulins, or other active agents for delivery, preferably site-directed delivery, to the site of a disease or disorder within the subject. In a further embodiment, the device allows the separate recovery of the target, either before or after modification, outside of the apparatus to be used in ex vivo assays or evaluations.

In another embodiment, the device can be used to capture the target component from the patient, and then the device can be removed from the patient and all manipulations of the apparatus, potentially including the modifications of the component that is captured, can take place in the sequestering chamber in the absence of the patient.

In another embodiment, physiological fluids may be removed from the patient by other means (for example, by withdrawing blood with a syringe, or by collecting plasma using a standardized method already employed by the industry) which can then be applied to the sequestering chamber via ports at valves (10) and (11), in the absence of the patient and in the absence of an extracorporeal circuit.

The apparatus of the invention may be used as a stand-alone system for processing physiological fluids, or other fluid feedstreams, and modifying components of the fluids, in the absence of the patient and in the absence of an extracorporeal circuit.

In an alternative embodiment, the complete apparatus of the invention may be formed by adopting a portion of an extracorporeal circuit that is already in place: for example, an apparatus may incorporate a partitioning chamber (e.g., a plasma separator) that is already in place and connected to a fluid source such as a patient. The remainder of the closed circuit for capturing and modifying a target component and then returning modified target component to the patient may be connected to the in-place partitioning chamber to complete the full apparatus of the invention.

The apparatus could be used to capture a target component from a closed circuit attached to a fluid-containing reservoir (for example, a bioreactor or perfusion bioreactor) for separation of the fluid (for example, cell culture supernatant or media) from unwanted components (for example, whole cultured cells) while returning the unwanted components back to the fluid-containing reservoir. The apparatus could be used to capture a target component from the fluid for modification or purification, and eventual return to the fluid-containing reservoir while maintaining a closed system, or for removal from the apparatus without exposing the target to adventitious agents in the environment.

The apparatus could be used to capture a target component from a circuit attached to a fluid-containing reservoir (for example, clarified or unclarified cell culture media supernatant) for separation of the fluid (for example, cell culture supernatant or media) from unwanted components (for example, whole cultured cells). The apparatus could be used to capture a target component from the fluid for modification or purification, and eventual removal from the apparatus.

In one embodiment of the invention, the targeted component is an antibody isolated from the plasma of whole blood withdrawn from a subject. The isolated antibody can be chemically or otherwise physically modified and reinjected back to the subject for therapeutic or diagnostic purposes. In this embodiment, the antibody may be present in the subject's circulatory system as a result of the presence of a disease state, e.g., tumor. In this particular instance, the antibody may be labeled, for example, with a radionuclide, by a conjugation reaction carried out within the circuit, then returned to the patient for site-directed monitoring to diagnose the precise location or locations of the tumor or other disease state. In another embodiment, the antibody may be conjugated with a radionuclide or with a drug or other cytotoxic component that is lethal to the tumor then reintroduced to the subject for site-directed delivery of the drug to the tumor site for treatment of the disease.

In yet another embodiment, the present invention is directed to a method for detecting or treating a disease or disorder, the method comprising withdrawing blood from a subject suffering from a disease or disorder into a closed circuit, wherein said disease or disorder causes the endogenous production of antibodies specific for diseased cells in the afflicted subject, separating the plasma from the cellular components of the withdrawn blood, isolating antibodies (including or restricted to antibodies specific for diseased cells) from the plasma, reacting the antibodies to conjugate them with a chemical component that renders the antibodies detectable or that is lethal or harmful to the diseased cells, then reintroducing the conjugated antibodies to the subject, wherein conjugated antibodies localize to the site of the diseased cells for detection and localization or for killing or attenuation of the diseased cells.

In one embodiment of the present invention, the method described herein will be performed with polyclonal antibodies withdrawn from the mammalian subject. In one embodiment, the method will be performed on antibodies specific for a single antigen. In one embodiment, the method will be performed on a population of antibodies exhibiting a certain characteristic, for example, type or class of immunoglobulin.

In another aspect, the apparatus of the present invention provides the means to capture and modify proteins from whole blood from the subject's circulation, and reinject the modified antibodies back into the patient, all within a closed system and without subjecting any blood components to the environment outside the subject's body. For example, specific antibodies present in a subject's circulation, i.e., bloodstream, as a natural response to a disease state, e.g., the presence of tumor antigens, can be withdrawn from the patient in whole blood and the antibodies specific for disease-related antigen(s) isolated, then the antibodies can be labeled with, for example, a radioisotope or conjugated with a therapeutic drug and returned to the patient and tracked to determine the precise location of the tumor or to deliver the therapeutic compound to the disease site. It will be appreciated that any of the myriad components that make up whole blood, e.g., proteins sugars, lipids, etc., can be targeted, isolated, and modified using the apparatus of the present invention prior to reinjecting the modified blood component back into the patient, all within a closed system. The apparatus can also be used to isolate and modify polyclonal antibodies that specifically recognize characteristic antigens associated with the patient's individual disease state. The apparatus can also be used to isolate and/or modify characteristic antigens associated with the patient's individual disease state.

An apparatus according to the invention can also be used to capture antibodies produced by a response to a vaccine or recognizing a known antigen or immunogen that had been previously introduced into the patient. These antibodies can then be labeled and re-introduced to the patient in order to monitor and evaluate the patient's humoral response to the vaccine, immunogen or antigen, or to localize to sites of antigen production or identify sites within the patient that are recruiting vaccine-induced antibodies. For example, the capture support could be funtionalized to display CD20 antigenic protein (or HIV envelope protein), allowing the capture of the patient's immunoglobulins that recognize this protein, for modification and reintroduction into the patient for diagnostic or therapeutic purposes.

The apparatus can also be used to capture antibodies of any class (IgM, IgG, IgE, etc.) or specificity for labeling and re-introduction to the patient for the purpose of identifying sites (for example, lymph nodes) of high traffic or association with the labeled antibodies.

The apparatus can also be used to capture and modify any target component from any fluid to examine the biological distribution in the patient.

The apparatus can also be used to capture antibodies associated with a patient's disease state for labeling and re-introduction to the patient for the purpose of identifying sites (for example, lymph nodes) of high traffic or association with the labeled antibodies.

The apparatus can also be used to capture target components associated with a patient's disease state for labeling and re-introduction to the patient for the purpose of identifying sites (for example, the thyroid) of high traffic or association with the labeled components.

The apparatus can also be used to capture antibodies associated with foreign entities, for example a vaccine, antigen, pharmaceutical or biologic for labeling and re-introduction to the patient for the purpose of identifying sites (for example, lymph nodes) of high traffic or association with the labeled antibodies.

The apparatus can also be used to capture antibodies associated with foreign entities, for example a vaccine, antigen, pharmaceutical or biologic for labeling and re-introduction to the patient for the purpose of evaluating the patient's humoral response to the foreign entity.

The apparatus can also be used to capture antibodies recognizing an antigen characteristic of a disease state, such as cancer (e.g., tumor-associated antigens), to allow visualization of the disease site for treatment by other means, such as external beam radiation therapy, or brachytherapy.

The apparatus can be used to capture any targeted component from the patient for coupling to a label or therapeutic, for example a pharmaceutical, biologic, or vaccine, in order to impart novel characteristics to the label or therapeutic, for example altered pharmacokinetics or absorption, distribution, metabolism and excretion profiles within the patient.

In another aspect, the present invention is directed to a method for detecting or treating a disease or disorder utilizing the novel extracorporeal closed circuit apparatus described herein.

The method comprises withdrawing a body fluid from a mammalian subject suffering from a disease or disorder, or suspected of suffering or having otherwise contracted a disease or disorder, isolating a target component associated with the disease or disorder from the withdrawn body fluid, modifying the target component, for example, to make the component capable of being monitored or otherwise tracked in vivo, or modifying the component to deliver a compound to a specific target site or target sites in vivo, and reinjecting the modified component back into the subject, wherein all these steps are carried out in a closed extracorporeal circuit connected to the body fluid circulation system of the subject. In another embodiment, the method comprises withdrawing blood from a subject suffering from a disease or disorder, the disease or disorder resulting in the production of endogenous antibodies specific for diseased cells in the afflicted subject, separating the plasma from the withdrawn blood, isolating antibodies from the plasma, labeling the antibodies with a compound, for example a radionuclide or radioisotope, reinjecting the labeled antibody and detecting the site(s) of the antigen associated with the disease or disorder that is recognized by the antibodies in the subject.

According to the method of the present invention, the isolated antibodies can also be utilized to treat the disease or disorder by labeling the antibody with a drug or cytotoxic substance for targeted delivery and release at the disease site. According to the method of the present invention, the isolated antibodies can also be utilized to treat the disease or disorder by labeling the antibody with an immunomodulator for the purpose of eliciting an activation or suppression response at the disease site. Modified antibodies can produce an agonist or antagonist effect on the patient's own immune response.

In one aspect, the isolated antibodies, following isolation and modification, can be utilized to determine the site or sites of a disease state, for example, a tumor, and monitor the spread or remission of the tumor following treatment. A particularly preferred method for detecting the site of a disease or disorder is via radioimaging where a particular molecule, e.g., an antibody, capable of binding to sites of disease (i.e., diseased cells) is covalently bound with a radionuclide or radioisotope, and the molecule is administered back into the patient and then tracked to the disease site or sites. Coupling a high energy radioactive molecule such as $^{125}$I or $^{90}$Y to immunoglobulins promotes the destruction of the tissue recognized by the immunoglobulins.

In yet another aspect, the apparatus of the invention could be used to detect metastatic cancer cells or sites of metastasis by labeling antibodies directed to the cells, which can then be administered back into the patient and then tracked to the disease site or sites.

The apparatus of the invention could also be used to detect metastatic cancer cells by using a suitable capture support that can bind and retain circulating tumor cells, which can then be labeled, or isolated from the apparatus for evaluation, or both.

In yet another aspect, a portion of the isolated antibodies may be removed from the apparatus, either before or after modification, and preserved. The isolated antibodies could later be introduced into the patient for imaging purposes to determine if the target of interest, for example cancerous tissue, is still present in the patient. This would be useful to determine, for example, if a disease is in remission, or to monitor progress of the disease over time. Alternatively, the isolated antibodies modified to impart a therapeutic effect, for example coupling a high energy radioactive molecule such as $^{125}$I or $^{90}$Y to immunoglobulins promotes the destruction of the tissue, could later be introduced into the patient with the intention of destroying the target, for example circulating tumor cells, cancerous tissue no longer in remission, or to destroy targets in metastasis.

Advantages

Accordingly, the present invention may have one or more of the following advantages:

The apparatus of the invention is designed as a closed system providing a circuit connected with a biological system (e.g., blood, lymph, spinal fluid systems) of a subject or a fluid system of a synthesis process (e.g., cell culture, reactor feedstream, bioreactor, etc.) into which samples (e.g., of body fluids or fluid media) can be diverted or drawn, within which components of the fluid samples may be separated out and specific target components within the fluid sample may be modified, and from which the fluid including modified components may be returned to the biological system of the subject or to the fluid system of a synthesis process for desired effects, all without fluid exiting the closed system and without being exposed to the environment outside the closed circuit.

For medical and veterinary applications, the novel apparatus of the invention provides a specialized extracorporeal circuit designed to remove and isolate a targeted blood component from a patient, modify the component, then return the modified blood component to the patient, without exposure of the targeted blood component to extracorporeal contaminants. The closed circuit system is simple and flexible in design and can make use of available materials and machinery. For example, the use of syringe pumps is especially optimal for embodiments of the present invention as they can readily be adapted to a closed system, they maintain measured, limited volumes for withdrawal and re-delivery, they are less subject to pulsation of flow and pressure, they are less prone to shear forces, and they do not subject the tubing or conduits of the apparatus to wear which could result in failure.

The apparatus can contain one or more capture supports at several isolated positions in the circuit. These capture supports may be of identical or different specificity and may rely on the same or different chemistry or configuration. By varying the type of capture support, multiple target components can be captured within the filtrate side of the circuit, for modification and subsequent introduction into a subject.

The apparatus itself can be sterilized, in whole or in part, e.g., using irradiation or ethylene oxide, prior to use. Alternatively, various parts of the apparatus may be separately sterilized or prepared using aseptic technique, for later assembly using sterile connections or aseptic techniques. For some purposes, components of the assembly do not need to be sterile, e.g., for purification of a target molecule from a cell culture bioreactor.

The apparatus may be flushed with an inert gas to minimize any reactivity of the components, for example cross linkers, that may be present.

A particular advantage of the apparatus of the present invention is the fact that the targeted component remains within the apparatus, i.e., within the closed circuit, for the entire process of withdrawal, isolation, modification, and reinjection, without the target component being exposed to the outside environment or manipulation from an external source. Hence the target component, and all fluids withdrawn from the mammalian subject for that matter, are always retained within the "closed circuit" and thereby screened or protected from any adventitious contamination, e.g., viral or bacterial infection, from outside the circuit.

The partitioning membrane also acts as a safety partition which isolates the contents of the sequestering chamber and prevents undesirable byproducts in the sequestering chamber, such as air or physical particulates that may be generated during the manipulation and modification of the target components, from entering the conduit that directly connects to the patient.

The apparatus can be disposable, and the entire circuit can be discarded after use, diminishing the chance of spreading blood-borne or body fluid-borne pathogens.

The apparatus may be operated with or without mechanical assistance, e.g., from syringe pumps, and can thus be put into operation in the absence of electrical power.

The apparatus, or any component of the apparatus, can be scaled during manufacture in order to accommodate and process a wide volume range, thereby allowing for the capture and/or modification of an increased or decreased proportion of the target component present in the patient.

The apparatus is also suitable for use on a wide range of animal species for therapy or diagnostic purposes. This function is additionally supported by the ability to scale the apparatus, or any component of the apparatus.

The device can be used to retain a sample of captured and/or modified target, or a subset thereof, for collection, screening, assays, or other types of ex vivo analysis.

The device can be used to provide a means to present a label such that it can be used for diagnostic visualization of a disease state.

The device does not require comprehensive modification of the target component, i.e., only a fraction of the total captured target component needs to be modified, in order to be effective.

In addition, the apparatus is minimally invasive and does not deplete the patient of physiologically significant proportions of non-targeted plasma molecules (for example: albumin or cytokines). It will be appreciated by one skilled in the art that the intention of the apparatus and method disclosed herein is not to deplete the patient of the component of interest, as in common apheresis methods, accordingly it is not necessary for the device to process a comprehensive volume of the patient's blood. This distinguishes the present invention in scope and action from common apheresis devices.

The limited processing volume of the apparatus reduces the propensity to create a thermocline in the body fluid, such as where a large volume of blood is diverted into an extracorporeal circuit with attendant loss of heat, for example, during kidney dialysis. If temperature control is required, the apparatus can readily accommodate this, e.g., through the use of heating blankets on the syringe, or by enclosing the apparatus in an incubating compartment during operation.

The apparatus can incorporate a safety valve to bypass the separation and reaction chambers of the circuit to allow the withdrawn body fluid to flow directly back to the patient without further processing of the withdrawn fluid. Such a safety bypass is useful for diminishing risk to the subject, for example, in case a breach occurs elsewhere in the circuit, or an adverse chemical reaction or overexposure of isolated targeted components occurs that makes them unfit for return to the subject. When the safety bypass is engaged all functional components of the apparatus are isolated from the patient without necessitating detachment of the apparatus from the patient.

The safety valve described may also be used to isolate the patient from the functional components of the apparatus during the initiation and/or completion of any processing steps, during evaluation of a processing step, or for a scheduled or unscheduled interruption of the procedure (for example, during a power outage, or for transfer of a patient).

The novel method allows that the removal, isolation, modification, and retransfusion of the targeted component occurs within the circuit and does not involve handling or direct manipulation of the patient's body fluid or the targeted component; thus, by utilizing the apparatus and methods disclosed herein, a high degree of sterility is maintained, and adulteration or introduction of contaminants is minimized to approximately the same level, or lower, as typically introduced by standard dialysis methods.

According to the apparatus and methods described herein, processed, modified target components are introduced to the patient by transfer across the partitioning membrane into the extracorporeal circuit, which allows for therapeutic or diagnostic molecules to be created in an isolated environment and introduced into the circulation system of a patient with minimally invasive techniques.

The apparatus and methods described herein may utilize polyclonal autoantibodies that have been produced by the patient's own immune system to specifically recognize the characteristics of the patient's individual disease state.

The apparatus and methods described herein may utilize polyclonal antibodies or other indicators of humoral response, that have been produced by the patient's own immune system to evaluate the patient's immune response to a previously introduced foreign entity, for example, an immunogen or vaccine, or a population of such agents.

The apparatus and methods described herein may be used to capture and potentially modify a previously introduced foreign entity, for example, an immunogen or vaccine.

The targeted component can be isolated from the fluid pathway and immediately purified using the device of the invention, allowing for the analysis or manipulation of transient or unstable molecules. Also, the targeted component can be isolated from the fluid pathway and immediately purified using the device, allowing for assessment or evaluation of the molecule in an expedited time frame.

Any physiological molecule can be captured and manipulated for diagnostic or therapeutic purposes by the defined apparatus, by altering the means of separating the target component from the physiological fluid or by altering the characteristics of the capture support used to immobilize the target molecule.

Using the apparatus of the invention, any component from any physiological fluid may be targeted for removal from the patient for ex vivo assays.

Using the apparatus of the invention, any component from any physiological fluid may be targeted, modified, and used for imaging, assessment, evaluation, monitoring, therapy, detection, or other related purposes.

The target component, i.e, the molecule or other element contained in a circulating fluid that the apparatus of the invention is designed to capture for modification, may actually be a complexed molecule involving two or more different molecules combined covalently or non-covalently. For example, the system may be designed to capture immune complexes from a patient. Such complexes may be separated into their component parts and one component (e.g., autoantibody, or antigen) modified and redirected to the patient.

The targeted component from the body fluid of a subject may be any molecule, protein, or other moiety contained in a body fluid that is capable of being partitioned and isolated, including, for example, whole cells, cellular components, or a virus, or any other physiological entity that can be isolated from the fluid pathway.

Using the apparatus of the invention, results based on the outcome of one procedure (for example, imaging) may be used to predict the effectiveness of further procedures (for example, targeted delivery of a modified target component to the disease site).

The apparatus and methods of the present invention may advantageously be used for the controlled introduction of external reagents into the physiological fluid that the apparatus is tapped into.

As the apparatus of the present invention enables the enhancement, reduction, or diagnostic evaluation of a subject's own immunoglobulin responses, which are in turn specific to the patient's own disease state, thus the apparatus allows for the creation and administration of targeted, patient-specific diagnostic reagents and therapeutics.

For example, coupling $^{111}$In to a patient's polyclonal antibodies will allow an imaging device such as a positron-emission tomography (PET) scanner to examine the distribution of the modified antibodies in the patient. Other known methods of scanning or "molecular imaging" may be used in conjunction with the methods and devices of the present invention, such as x-ray computed tomography (CT), magnetic resonance imaging (MRI), functional magnetic resonance imaging (fMRI), ultrasound, gamma camera, and single photon emission computed tomography (SPECT).

Using the apparatus of the invention, a variety of radioisotopes, including isotopes of technetium, indium, copper, rhenium, gold and arsenic may be used to label targeted components such as proteins, including antibodies.

Using the apparatus of the invention, antibodies and other body fluid components may be conjugated with a variety of radionuclides for potential use in targeted immunotherapy.

These radionuclides may include, but are not limited to, $^{131}$I, $^{125}$I, $^{123}$I, $^{99m}$Tc, $^{67}$Ga, $^{90}$Y and $^{111}$In.

Modification of immobilized antibodies is also contemplated using the methods and devices of the present invention. For some purposes, it may be advantageous to cleave whole antibodies into smaller antibody fragments within the closed circuit, e.g., so as to produce Fab' fragments, F(ab')$_2$ fragments or Fv fragments. An antibody immobilized in the sequestering chamber of the apparatus of the present invention may be treated with any number of enzymes or chemicals known in the art, for example, papain, either before or after any other modification step, to remove a portion of the antibody, such as constant domains, while retaining one or more antigen binding domains.

The methods and apparatus of the invention may be used for other modifications of immobilized target components including but not limited to peptide cleavage, deglycosylation, oxidation, reduction of disulfide bonds, protein refolding, cross-linking, aggregation, or hydrolysis.

According to the methods of the present invention, a component of a patient's own physiological system may be transformed as a vehicle for delivering a therapeutic or imaging compound to the patient, with the subsequent outcome of improved or altered pharmacokinetics (PK) or absorption, distribution metabolism and excretion (ADME) profile.

The novel apparatus provides a specialized closed circuit designed to remove and isolate a targeted biological component (for example, a recombinant antibody) from a fluid-containing system (for example, a bioreactor or perfusion bioreactor), and return either the targeted component or the remainder of the depleted fluid back to the fluid-containing system, without compromising the closed system.

The novel apparatus provides a specialized circuit designed to purify and potentially modify a targeted component from a fluid (for example, harvested cell culture media) either by manual or automated procedures, within a closed or open system environment.

The apparatus may be modified to allow operation in the absence of the partitioning chamber, or in the absence of the membrane in the partitioning chamber, allowing the whole fluid to be diverted to the sequestering chamber directly without separation or modification.

Accordingly, in its broadest aspects novel apparatus are provided which can be characterized as follows:

The invention provides an extracorporeal closed-circuit apparatus comprising:

(a) an inlet for accessing the body fluid of a mammalian subject;

(b) a sequestering chamber connected to said inlet which allows passage of said body fluid into said sequestering chamber, said sequestering chamber comprising a capture support capable of binding to or reacting with a targeted component of said body fluid upon contact with the capture support; and (c) an outlet for accessing the body fluid circulatory system of said mammalian subject and introducing body fluid exiting said sequestering chamber into said subject; wherein said inlet, sequestering chamber, and outlet are connected in series to provide a closed circuit. This apparatus may advantageously also comprise a partitioning chamber connected between said inlet (a) and said sequestering chamber (b), where said partitioning chamber provides means for fractionation of said body fluid, and wherein said inlet, partitioning chamber, sequestering chamber, and outlet are connected in series to provide a closed circuit, and said sequestering chamber is connected to said partitioning chamber so that a fraction of said body fluid containing targeted component is conducted from said partitioning chamber to said sequestering chamber.

The apparatus described above may have the partitioning chamber that is comprised of a filtering means which allows passage of a targeted component of said body fluid to produce a filtrate while retaining other components of said body fluid, and wherein said sequestering chamber is connected to said partitioning chamber so as only to receive filtrate. In further embodiments, the sequestering chamber comprises an inlet line connected to said partitioning chamber so as to receive fluid flow from the filtrate side of said filtering means and further comprises an outlet line connected to said partitioning chamber so as to conduct fluid flow from said sequestering chamber to the filtrate side of said partitioning chamber. The connections between the inlet, partitioning chamber (where present), sequestering chamber and outlet may advantageously be equipped with appropriate valving to regulate flow of fluid through the system.

An apparatus according to the invention may be designed to access fluid media from a bioreactor or synthesis feedstream, instead of accessing body fluid from a living subject. In such embodiments, the invention provides a closed diversion circuit apparatus comprising:

(a) an inlet for accessing a fluid medium in a bioreactor;

(b) a sequestering chamber connected to said inlet which allows passage of said fluid medium into said sequestering chamber, said sequestering chamber comprising a capture support capable of binding to or reacting with a targeted component of said fluid medium upon contact with the capture support; and (c) an outlet for accessing the bioreactor and introducing bioreactor fluid exiting said sequestering chamber into said bioreactor;

wherein said inlet, sequestering chamber, and outlet are connected in series to provide a closed circuit. In such a diversion circuit, it may be advantageous also to include a partitioning chamber connected between said inlet and said sequestering chamber, said partitioning chamber providing means for fractionation of said fluid medium, wherein said inlet, partitioning chamber, sequestering chamber, and outlet are connected in series to provide a closed circuit, and said sequestering chamber is connected to said partitioning chamber so that a fraction of said body fluid containing targeted component is conducted from said partitioning chamber to said sequestering chamber.

In further embodiments, the partitioning chamber is comprised of a filtering means which allows passage of a targeted component of said fluid to produce a filtrate while retaining other components of said fluid, and wherein said sequestering chamber is connected to said partitioning chamber so as only to receive filtrate.

In particular embodiments, an extracorporeal closed-circuit apparatus is provided comprising:

(a) an inlet for accessing the body fluid of a mammalian subject;

(b) a partitioning chamber comprising filtering means which allows passage of a targeted component of said body fluid to produce a filtrate while retaining other components of said body fluid;

(c) a sequestering chamber comprising a capture support capable of binding to or reacting with said targeted component upon contact with the filtrate; and (d) an outlet for accessing the body fluid circulatory system of said mammalian subject and introducing body fluid exiting said partitioning chamber into said subject;

wherein said inlet, partitioning chamber, sequestering chamber, and outlet are connected in series to provide a closed circuit, and said sequestering chamber is connected to said partitioning chamber so as only to receive filtrate.

Another embodiment of this invention relates to a closed diversion circuit apparatus comprising:

(a) an inlet for accessing a fluid medium in a bioreactor;

(b) a partitioning chamber connected to said inlet comprising filtering means which allows passage of a targeted component of said bioreactor fluid to produce a filtrate while retaining other components of said fluid;

(c) a sequestering chamber connected to said partitioning chamber comprising a capture support capable of binding to or reacting with said targeted component upon contact with the filtrate; and (d) an outlet for accessing the bioreactor and introducing bioreactor fluid exiting said partitioning chamber into said bioreactor;

wherein said inlet, partitioning chamber, sequestering chamber, and outlet are connected in series to provide a closed circuit, and said sequestering chamber is connected to said partitioning chamber so as only to receive filtrate.

In the foregoing embodiments, said sequestering chamber may comprise an inlet line connected to said partitioning chamber so as to receive fluid flow from the filtrate side of said filtering means and may further comprise an outlet line connected to said partitioning chamber so as to conduct fluid flow from said sequestering chamber to the filtrate side of said partitioning chamber. The apparatus will also advantageously include valves in said inlet and outlet lines and connecting lines whereby fluid flow between said partitioning chamber and said sequestering chamber may be regulated or stopped.

The apparatus of the invention may also advantageously comprise one or more pumping means capable of driving fluid flow through said circuit. The pumping means may be capable of driving fluid flow in the direction of the outlet or alternatively in the direction of the inlet. Suitable pump means may include a syringe pump, peristaltic pump, piston pump, diaphragm pump, combinations thereof, and the like.

In particular embodiments, the partitioning chamber will include filtering means having a pore diameter of from 0.05 to 1 µm. In some embodiments, said filtering means have a pore diameter of from 0.05 to 0.2 µm. Suitable filtering means will include hollow fiber membranes, flat sheet membranes, membrane cassettes, rolled sheet membranes, and the like.

The closed circuit apparatus according to the invention may also advantageously include compartments suitable for the storage of chemicals and solutions, wherein said compartments are connected to said partitioning chamber and/or said sequestering chamber, said connections comprising valves for regulating the flow of chemicals and solutions between said compartments and said chambers. The connections between chambers of the apparatus and to any peripheral compartments may include in-line filters to prevent contamination.

The apparatus of the invention may also advantageously be equipped with at least one injection port suitable for introducing a reagent into the closed circuit of said apparatus.

In an embodiment, in the sequestering chamber, the capture support comprises a solid support having antibodies, antibody fragments, binding peptides, or aptamers immobilized thereon which are reactive with or bind one or more targeted components. In particular embodiments, the capture support comprises Protein A or Protein G, which are suitable for capturing an antibody targeted component.

Particular embodiments of the apparatus of the invention will comprise a conduit connecting said inlet and said outlet, said conduit further comprising a safety valve for directing said withdrawn body fluid or diverted fluid media directly back to the source (e.g., mammalian subject, bioreactor, fluid stream), thereby bypassing the partitioning chamber, sequestering chamber and the rest of the closed circuit.

The invention also provides a method for enhancing the body fluid of a subject comprising:

(a) conducting a body fluid from a mammalian subject into an extracorporeal closed circuit comprising (i) an inlet; said inlet being connected to (ii) a partitioning chamber comprising filtering (or fractionation, seperation, etc.) means which allows passage of a targeted component of said body fluid to produce a filtrate while retaining other components of said body fluid, said partitioning chamber being connected to (iii) an outlet for returning body fluid to said mammalian subject; and (iv) a sequestering chamber comprising a capture support capable of binding to or reacting with said targeted component upon contact with the filtrate; wherein said sequestering chamber is connected to said partitioning chamber so as only to receive filtrate from the partitioning chamber or to return filtrate to the partitioning chamber;

(b) conducting filtrate into said sequestering chamber, whereby at least a portion of said targeted component in said filtrate is bound to or undergoes a modification reaction with said capture support;

(c) optionally carrying out a further modification (e.g., a chemical reaction) in said sequestering chamber to modify at least a portion of said targeted component;

(d) conducting modified targeted component from said sequestering chamber to said partitioning chamber or to said outlet; and (e) reintroducing body fluid retentate emitting from said partitioning chamber and modified targeted component into said subject.

Alternatively, the invention provides a method for detecting or treating a disease or disorder causing the endogenous production of antibodies specific for diseased cells in a subject comprising:

(a) conducting blood from a mammalian subject suffering from a disease or disorder into an extracorporeal closed circuit comprising (i) an inlet; said inlet being connected to (ii) a partitioning chamber comprising filtering means which allows passage of said antibodies of said blood to produce a filtrate while retaining other components of said blood, said partitioning chamber being connected to (iii) an outlet for returning said blood to said mammalian subject; (iv) a sequestering chamber comprising a capture support capable of binding to or reacting with said antibodies upon contact with the filtrate; wherein said sequestering chamber is connected to said partitioning chamber so as only to receive filtrate from the partitioning chamber or to return filtrate to the partitioning chamber;

(b) conducting said filtrate into said sequestering chamber, whereby at least a portion of the antibodies in said filtrate are bound to or undergo a modification reaction with said capture support;

(c) carrying out a further chemical reaction in said sequestering chamber to modify at least a portion of said antibodies, wherein said modified antibodies are rendered detectable or lethal to said diseased cells as a result of said chemical reaction;

(d) conducting the modified antibodies from said sequestering chamber to said partitioning chamber or to said outlet;

(e) reintroducing blood retentate emitting from said partitioning chamber and said modified antibodies into said subject; and (f) monitoring the target of said antibodies to determine the disease site or lethality of said modified antibodies with respect to said diseased cells.

Alternative methods may also be devised for extracting fluid from a non-living vessel, such as a bioreactor or synthesis feedstream, capturing and modifying a targeted component, and returning the modified component back to the vessel from whence it was extracted, by following similar steps and employing an apparatus such as described above. In such methods, if fractionation or filtering of the extracted fluid is not required, the method steps do not have to include the use of a partitioning chamber.

From the foregoing description, it will be apparent that the methods and apparatus of the invention can be modified to provide a means to visualize the biodistribution of the targeted component for diagnostic purposes.

The method and apparatus of the invention may be used as a means to impart a new or novel function to the targeted component, such as a vehicle for the modifier, an imaging agent, an immunomodulator, a therapeutic, etc.

The method and apparatus of the invention may be used as a means to impart new or novel function to the modifier, such as enhanced PK or ADME.

The method and apparatus of the invention may be used a means to evaluate the method as a candidate for targeted therapy or site directed delivery.

The method and apparatus of the invention may be used for monitoring humoral response to a disease state, vaccine, immunogen, or antigen.

The method and apparatus of the invention may be used for visualization of a disease site as a guide for external therapy such as radiotherapy.

The method and apparatus of the invention may be used as a means to destroy metastatic cancer cells.

The method and apparatus of the invention may be used as a means to capture and/or modify foreign entities such as pharmaceuticals or vaccines.

The method and apparatus of the invention may be used to image disease progression or remission.

The method and apparatus of the invention may be used to permit visualization by methods such as PET, NMR, etc.

The method and apparatus of the invention may be used as a means for isolation and removal of the targeted component, before or after modification, for analytical purposes.

The method and apparatus of the invention may be used as a means to process media from cell culture or bioreactors for isolation and removal of the targeted component, before or after modification, for analytical purposes or animal studies.

The method and apparatus of the invention may be used as a means to image and destroy cancer tissue.

The apparatus and methods of the present invention will be further understood by reference to the drawings provided and the description below.

DEFINITIONS

Figure 1:
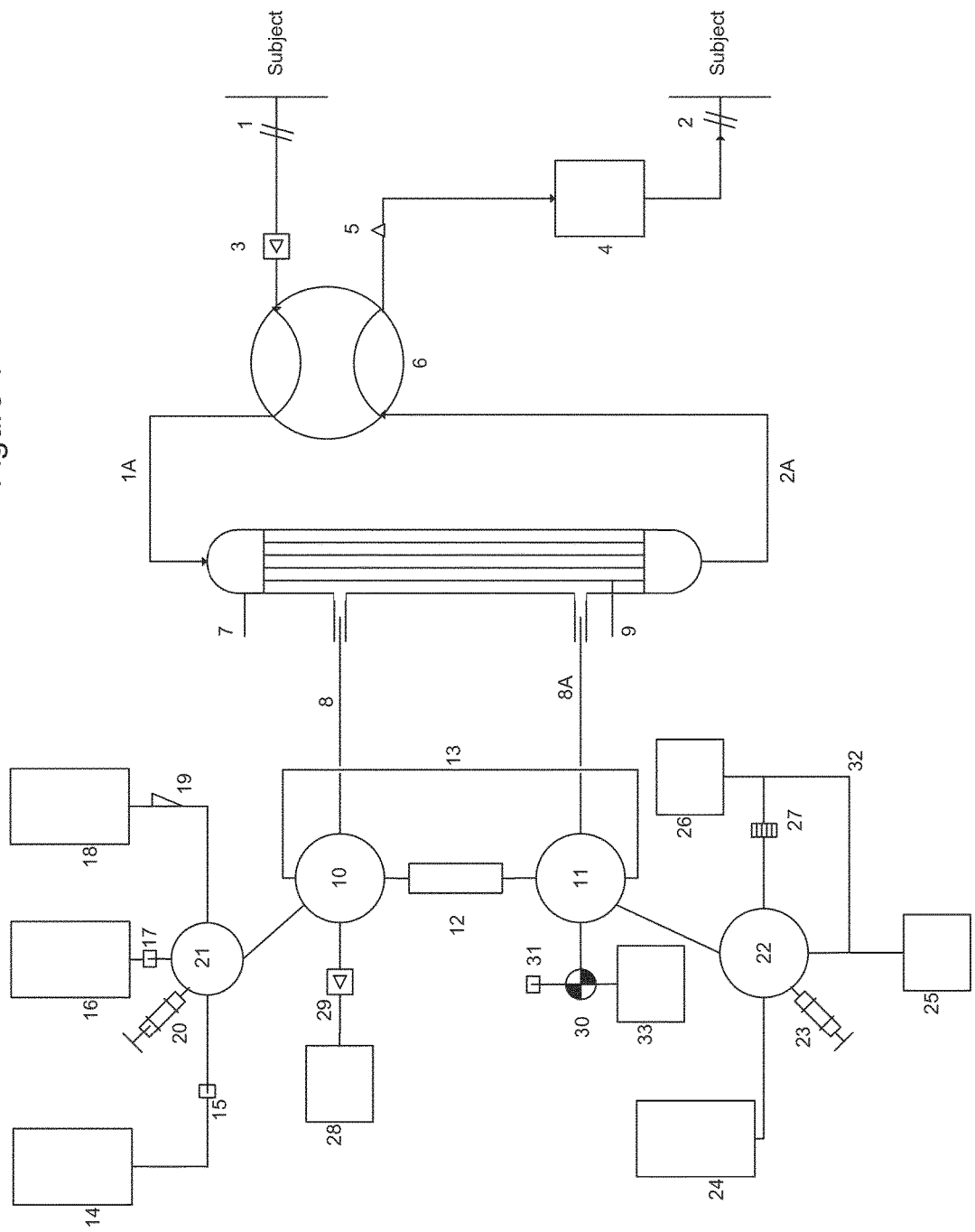
FIG. 1 is a schematic diagram of one embodiment of an apparatus of the present invention.

The term "closed-circuit apparatus" or "closed circuit" as used herein refers to a fluid path or channel initiating from an inlet, connecting through various chambers, and ending with an outlet, which, when the inlet and outlet are connected to a circulatory system of a mammalian subject, forms an extracorporeal pathway that is not open to the surrounding environment and maintains the integrity of any of the subject's body fluid introduced into the circuit and reintroduced to the subject, unless the operator of the closed circuit causes separation and/or modification reactions to be performed on the body fluid circulating through the circuit in accordance with the methods described herein. The inlet of a closed circuit in the context of the invention will typically be a catheter connected to a circulatory system in a mammalian subject, e.g., circulating blood connected via an intravenous or intraarterial needle, for withdrawal of a body fluid, e.g., blood, into the closed circuit and terminating at the outlet which will typically be a catheter reconnecting to the circulatory system of the mammalian subject whereby the subject's body fluid drawn into the circuit via the inlet and optionally treated in accordance with the methods of the present invention, may be reintroduced into the subject. The term will also apply to a fluid path or channel where the inlet and outlet are connected to another closed system, such as a bioreactor vessel.

The term "extracorporeal" as used herein refers to a process or procedure performed outside the body. While extracorporeal circuits are described herein for removing a body fluid component from a living subject, it will be understood that the term can also be used to describe a diversion circuit from a bioreactor or other vessel or circulation system that does not involve a living source for a fluid to be sampled and components thereof to be captured and modified, then returned to the source.

The term "target", "target component", "targeted component", "target molecule", or "targeted molecule" as used herein refers to any biomolecule, protein, cell, cell fragment, nucleic acid, virus or other substance that is present in the mammalian subject, in for example, the subject's body fluid, and can be isolated from a body fluid of the mammalian subject. The target or targeted component, etc., will be the object of isolation and modification processes conducted within the closed circuit apparatus according to the present invention. One example of a target as contemplated by the present invention, would be an antibody present, for instance in the blood of the subject. Another example of a target as contemplated by the present invention, would be a heterogeneous or a homogenous complex of molecules, associated by covalent or non-covalent bonding, for example, an antibody/antigen complex or an antibody bound to a cell.

The "target" may also include a biomolecule produced in a cultured cell media as described above. The "target" may also include a foreign component that is not native to the patient, e.g., an antigen, vaccine or pharmaceutical, which has been introduced to the patient by external means including injection, inhalation or ingestion.

The term "modified" or "modification" as used herein refers to any known alteration that can be performed on a biomolecule or other targeted component isolated from a body fluid of a subject mammal such that the altered biomolecule or component exhibits a new property or activity when reinjected into the subject. Examples of modifications include, for example, the covalent attachment of a detectable label (e.g., such as a radioisotope) or an active agent (e.g., such as an enzyme or chemotherapeutic agent) to a blood component (e.g., an antibody) isolated from a subject, or the deglycosylation of the targeted molecule. Modification can involve the non-covalent attachment of a label or therapeutic to the target component.

The term "capture support" as used herein refers to any solid surface or matrix (polymer, gel, silica, polyethersulfone, cellulose acetate, agarose, acrylamide, etc.), which may be porous or non-porous, and which may have surface modifications to impart enhanced properties (such as ionic, hydrophobic, affinity, etc.), which capture support exhibits a surface moiety (e.g., an affinity ligand, adsorbant, binding partner for a particular target, etc.) enabling the capture support to bind to or chemically react with one or more target components coming into contact with the capture support. The surface of a capture support may present features which are recognized by the patient's immune system, such as by the presentation of a peptide, protein, pharmaceutical biologic, or vaccine, to which immune effector molecules are reactive. The capture support may be coated with a protein or antigen which activates a target component, for example, where B cells are exposed to an antigen immobilized on the capture support, which antigen is associated with a disease against which the subject has been vaccinated.

The term "antibody", as used herein, broadly refers to any immunoglobulin (Ig) molecule comprised of multiple polypeptide chains, including heavy (H) chains and light (L) chains, or any functional fragment, mutant, variant, or derivative thereof, which retains the essential epitope binding features of an Ig molecule. Such mutant, variant, or derivative antibody formats are known in the art. In a full-length antibody, each heavy chain is comprised of a heavy chain variable region and a heavy chain constant region. The heavy chain constant region is comprised of three domains, CH1, CH2 and CH3. Each light chain is comprised of a light chain variable region and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

A device or method described herein as "comprising" one or more named elements or steps is open-ended, meaning that the named elements or steps are essential, but other elements may be added within the scope of the device or method. To avoid prolixity, it is also understood that any apparatus or method described as "comprising" (or which "comprises") one or more named elements or steps also describes the corresponding, more limited apparatus or method "consisting essentially of" (or which "consists essentially of") the same named elements or steps, meaning that the apparatus or method includes the named essential elements or steps and may also include additional elements or steps that do not materially affect the basic and novel characteristic(s) of the apparatus or method. It is also understood that any apparatus or method described herein as "comprising" or "consisting essentially of" one or more named elements or steps also describes the corresponding, more limited, and closed-ended apparatus or method "consisting of" (or which "consists of") the named elements or steps to the exclusion of any other unnamed element or step. In any composition or method disclosed herein, known or disclosed equivalents of any named essential element or step may be substituted for that element or step.

The term "partitioning chamber" refers to the component or components of the apparatus designed to separate fluids comprising the target from a comprehensive whole fluid.

The term "sequestering chamber" refers to the component or components of the apparatus designed to capture and modify the target or targets isolated from the comprehensive whole fluid.

The term "whole fluid" refers to the starting material drawn into the apparatus.

In one embodiment, the sequestering chamber itself may be a closed system independent of the partitioning chamber under circumstances where the membrane in the partitioning chamber defines it as such.

DETAILED DESCRIPTION OF THE INVENTION

A closed circuit apparatus of the present invention comprises, in its most basic aspects, an inlet, a partitioning chamber, a sequestering chamber, and an outlet, all connected via channels or conduits providing a continuous fluid flow path from the inlet, through the partitioning and sequestering chambers, to the outlet. Valves and optional additional channels are provided to control access of fluid flow to the respective chambers or to bypass the chambers and create a direct circuit from inlet to outlet. Additional chambers, reservoirs, channels and valves may be added to the closed circuit for selective and controlled introduction of additional elements, such as reactants, eluants, buffers, diluents, and the like, into the system, typically into the sequestering chamber, to carry out the modification reaction(s) on an isolated target component drawn into that part of the circuit. One or more pumps may be attached to the circuit to conduct the fluid flow through the circuit, that is, if sufficient flow through the circuit is not provided by gravity or fluid pressure (e.g. blood pressure) when the circuit is open to the circulatory system of the mammalian subject.

The inlet is a means for accessing and withdrawing a portion or sample of a body fluid from a subject, for example, a catheter for accessing and withdrawing blood from the blood circulatory system of a subject. The withdrawn body fluid is then conducted through the circuit to the partitioning chamber for further processing. Optionally, the circuit may include a valve, e.g., safety valve, prior to the partitioning chamber, which redirects flow from the inlet directly to the outlet, and thence to the circulatory system of the subject, thereby bypassing the partitioning chamber and other components of the circuit. In alternative embodiments, the inlet and outlet could connect to any fluid source (not limited to body fluids of a living subject), for example, to a bioreactor.

The partitioning chamber is comprised of a separator, or filtering means such as a dialyzer, for partially fractionating the body fluid entering the chamber into at least two portions, one portion containing a target component which portion penetrates the filter (filtrate) and one portion which does not penetrate the filter (retentate) and proceeds through the circuit toward the outlet. The filtering means may be any type of filter capable of permitting passage of the target component, although it will be appreciated that it is not critical that all of the target in a fluid sample entering the partitioning chamber must pass through the filter; target components in the retentate will simply return to the subject without modification. Suitable filtering means include, e.g., hollow fiber membranes, flat sheet membranes, membrane cassettes, rolled sheet membranes, and the like, and may be comprised of any material known in the art for the filtration of biological fluids, e.g., glass fiber filters, silicon, microporous membranes, etc. A suitable filter will be a porous membrane designed to allow a targeted component from the body fluid to flow through the membrane while preventing or retaining other or unwanted components. For example, in a circuit designed to receive blood, one embodiment will utilize a porous membrane able to separate blood components on the basis of size or molecular weight, such as a hollow fiber membrane permitting plasma and its constituent components to pass through (filtrate) but preventing cellular components and platelets from being transported across the membrane (retentate). In preferred embodiments, the pore size of the porous membrane housed in the partitioning chamber is 0.2 micron or less and is composed of polyethersulfone. The retentate can be directly conducted to the outlet and injected back into the subject.

Filtrate collected in the partitioning chamber may be conducted to a sequestering chamber where targeted component(s) of the filtrate can be isolated and modified. Appropriate valving and conduits, and as necessary pumping means, are provided for the selective transmission of filtrate from the partitioning chamber to the sequestering chamber and from the sequestering chamber to the partitioning chamber or outlet, optionally via a holding or remixing reservoir. The sequestering chamber comprises a capture support capable of specifically binding or immobilizing a target. The capture support may utilize any suitable technology or chemistry for complexing target molecules. Targets may be immobilized by affinity interaction with binding moieties on the support such as antibodies, antibody fragments, binding peptides, aptamers, etc., or by chemical reaction or interaction with the support such as by hydrophobic interaction, conjugation reactions or cross-linking, and the like. For example, in embodiments where the targeted component of a subject's body fluid is IgG antibodies, the capture support in the sequestering chamber can advantageously be comprised of Protein A or Protein G, which effectively capture and isolate IgG target molecules. The capture support may be a membrane, porous bead, non-porous bead, packed bed, gel, or any modified surface. The targeted component does not necessarily have to penetrate through the capture support, as long as it contacts the capture support.

The sequestering chamber is preferably equipped with one or more ports or connections to additional chambers or reservoirs for the selective introduction of additional materials into the sequestering chamber, e.g., for interaction with the isolated target. If the modification designed to take place in the sequestering chamber may be performed without the addition of further reagents, then such additional ports or connections are not mandatory, however in cases where a multistep treatment is intended for the immobilized target, then additional connections, reservoirs, and appropriate valving and pumping means will be useful. For example, in a closed circuit designed to alter a particular chemical target, the capture support may simply contain a catalyst or chaotropic agent effective to alter the target component as desired as it passes through the chamber; in such a case, no additional modification steps may be necessary and introduction of additional reagents to the sequestering chamber is not needed. In other cases, a closed circuit according to this invention may be designed for modifying a target component physically, for example by altering a target protein's glycosylation or by conjugating the target with another moiety such as a detectable label or cytotoxic moiety, in which case the target may need to be captured and subjected to a series of chemical reactions, including washings, before being eluted and conducted out of the sequestering chamber toward the outlet of the circuit. In those embodiments requiring a series of reactions or modification steps conducted in the sequestering chamber, additional ports or connections to reservoirs for introduction of reagents and reactants needed in the modification may be required.

Ports and additional connections leading into the sequestering chamber are designed to preserve the closed circuit of the system. Thus, ports for introduction of additional chemicals or fluids may be airtight and watertight septums through which sterile syringe needles may be inserted. Likewise, the connecting conduits and reservoirs are added to the system via sterile connections and utilize sterile filtered vents to maintain the circuit as closed to the outside environment and uncontaminated. The steps of any modifying reaction may be carried out in the sequestering chamber isolated from the flow of body fluid through the circuit. Retentate proceeds through the partitioning chamber and to the outlet without reaching the sequestering chamber, and once targeted components of the filtrate have been captured in the sequestering chamber, the channels between the partitioning chamber and the sequestering chamber may be closed, so that no flow back to the partitioning chamber or to the outlet from the sequestering chamber takes place. The ability to close off the sequestering chamber from the retentate side of the circuit protects the flow returning to the subject from incorporating any unwanted materials, reactants, or byproducts of the modification reactions that take place in the sequestering chamber.

A reaction to modify a captured target may require several steps and utilize several different reagents. For example, where the capture support is an affinity capture support coated with Protein A, IgG targets will be immobilized on the support when a fluid containing IgG is introduced into the sequestering chamber. The immobilized IgG may then be washed with a buffer introduced into the sequestering chamber, e.g., to remove other filtrate components that might interfere with the modification reaction(s). After washing, a reactant such as a radiolabeled conjugating moiety capable of reacting with the immobilized IgG is introduced into the sequestering chamber and any additional reagents or reaction conditions such as heat or UV irradiation are introduced to cause the conjugation of the radiolabel to the immobilized target to take place. After removal of the non-immobilized reactants from the chamber, washing solutions may be introduced to remove any unbound or unconjugated materials, then after removal of the washing solution, introduction of an eluant or altering conditions of the sequestering chamber to release the captured target IgG (now modified, e.g., by radiolabel). The sequestering chamber may then be reconnected to the retentate side of the circuit by opening a channel leading from the sequestering chamber back to the partitioning chamber, directly to the outlet, or to an optional intermediate chamber such as a remixing/reheating chamber. Preferably, the modified target released from the sequestering chamber is directed back to the partitioning chamber, where it passes through the same filtering means by which it entered the filtrate side of the circuit; from there the modified target component remixes with the retentate and proceeds in the direction of the outlet.

The apparatus preferably further comprises one or more compartments attached or removably attached to the apparatus for storing solutions or other components used in the process of isolating, modifying, and returning the target molecule to the subject. Referring to FIG. 1, an embodiment of the apparatus of the invention is shown which is adapted to receiving blood from a subject, modifying a blood component, and returning the modified component back to the subject. The apparatus of FIG. 1 features an inlet connection (1) communicating with a circulatory system of a mammalian subject and an inlet line (1A) leading from the subject to a partitioning chamber (7) housing a separator filter (9), e.g., a 0.1 µm pore size hollow fiber membrane filter, which partitioning chamber (7) is connected to a sequestering chamber (12) via line (8), which in turn reconnects to the partitioning chamber (7) via line (8A), and which partitioning chamber connects to an outlet line (2A) leading back to a circuit outlet connection (2) communicating with the subject's circulatory system. The partitioning chamber (7) encloses a separator comprising, e.g., a hollow fiber membrane (9) which creates a filtrate side and a retentate side to the system. Retentate flows through the partitioning chamber (7) to the outlet line (2A) and the outlet connection (2) to the subject. Filtrate is in communication with the sequestering chamber via lines (8) and (8A). The system is equipped with appropriate valves: check valve (3) on the inlet connection (1); safety valve (6) to create a bypass circuit directly to the outlet (2); 4-way selector valves (10, 11, 21, 22) to create a controllable circuit feeding into and emptying the sequestering chamber (12). As illustrated in FIG. 1, the flow through open circuits of the system is driven using syringe pumps (20 and 23). On the filtrate side of the circuit (i.e., the portion of the circuit accessible only to filtrate and not retentate), a variety of inputs and connections leading to or from the sequestering chamber are shown: compartments for water (14), buffer (16) such as PBS, and buffer or dry chemicals (18) are illustrated with connections through valves (21 and 10) to the sequestering chamber (12). Compartments (24, 25, 26, 28, 33) for waste, collection or mixing of materials after passage through the sequestering chamber (12) or for side mixing or holding are also connected through selector valves (10, 11, and 22) to the sequestering chamber; additional valves such as check valve (29) and 3-way valve (30) are provided which prevent or allow control over return of material to the circuit. A drip chamber (4) is illustrated in the line leading to the outlet (2). Other features are illustrated which may be useful in a circuit for withdrawing and treating blood drawn from a subject, including a port (5) for introduction of anticoagulant, an injection port (19), and a sample port (31) which can be used to withdraw samples for monitoring the reaction in the sequestering chamber via, for example, an assay, or to preserve samples of the labeled or unlabeled target. A bypass line (13) for creating a pathway bypassing the sequestering chamber or isolating the sequestering chamber (12) is also provided. An optional bypass line (32) between peripheral collection chambers (25, 26) is illustrated. Various lines are further protected from introducing contaminants, particles, aggregates or precipitates into the system by various filters (15, 17, 27), e.g., 0.2 µm membrane filters.

As seen in FIG. 1, each compartment is in communication via a conduit connection with the apparatus such that the contents of any one compartment, for example, wash buffer, can be easily directed to any section of the apparatus by selectively adjusting any of the 4-way selector valves (10, 11, 21, 23) and operation of the syringe pumps (20, 23). For example, after binding of the target component to the capture support in the sequestering chamber, one compartment (16) containing dry PBS can be reconstituted to produce a wash buffer by the addition of water-for-injection (WFI) contained in a second compartment (14). Once reconstituted, the PBS can then be directed to the sequestering chamber and contact with the capture support to remove any unbound target and other components, for example plasma protein, from the sequestering chamber (12). The wash buffer can then be directed to a waste compartment (33) for removal. Once the support has been washed, the label, drug, etc., can be added to the apparatus for interaction with the target molecule as described above. The support can be similarly washed again. Following this step, an elution buffer can then be directed to the sequestering chamber (12) to contact and elute the modified target molecule from the affinity capture support. Once the target molecule has been eluted from the capture support, the solution comprising the target molecule can be directed to a compartment (25) containing a neutralization buffer, e.g., HEPES, preparatory to returning the target molecule to the patient. From the neutralization compartment (25) the target molecule can then be transferred either to a secondary holding compartment (26) or directly back to the partitioning chamber (7), then on to outlet line (2A) and the outlet (2) for return to the subject's circulatory system.

The 4-way selector valves (21, 22) are configured such that the syringes (20, 23) are connected at the bottom face of the valve (along the "z" axis). A single channel is configured such that one end of the channel is always in connection with the syringe. The channel then turns at a right angle such that the other end can be placed in communication with either of the outlets located at 0 degrees, 90 degrees, 180 degrees and 270 degrees as shown in the drawings. Note that valves (10) and (11) are similarly structured, with the connection at 180 degrees from valve (21) connecting to the bottom face of valve (10), and the connection at 0 degrees from valve (22) connecting to the bottom face of valve (11). Note also that these valves could easily be redesigned to select any number of ports, for example, as a 6-way selector valve.

All lines and conduits making up the fluid path within the closed circuit apparatus are preferably comprised of biologically inert, medical-grade tubing of the appropriate diameter and wall thickness. The tubing may be manufactured from any material known in the art that is suitable for medical applications, for example, polyethylene, polypropylene, polycarbonate, etc., and any component of the fluid path can be machined or injection molded, or comprised of etched or stamped fluid paths suitable for milliliter, microliter and nanoliter volumes. The lines may also be composed of C-flex tubing capable of sterile connection using a Sterile Connection Device (SCD).

The fluid path within the fully assembled apparatus is configured such that the only connections outside of the closed system are at the catheter access points (1, 2) of the subject's circulatory system. These connection points may also be made from alternate components, including, but not limited to, luer fittings, rubber septums, hosebarbs or sealed ends. It is desirable, but not required, that these connection points be sterile and are able to be connected to the patient or fluid source without compromising sterility. Peripheral connections to detachable reservoirs and compartments, such as sterile water-for-injection (14) are preferably isolated from the closed system by sterilizing filters (15), but may incorporate alternate components or means of sterile connection.

The present invention provides a method particularly well suited for withdrawing whole blood from a mammalian subject, isolating a blood component from the withdrawn sample, chemically modifying the isolated blood component, and returning the modified component to the subject, all within a closed extracorporeal circuit that does not expose the withdrawn blood to the environment or outside contamination. The component may be chemically or otherwise physically modified while isolated in the apparatus prior to return of the component, now modified, into the subject. However, while the devices and methods disclosed herein are well suited to isolation and modification of one or more components of blood, for example proteins such as antibodies or particular subpopulations of antibodies, it will be understood by those skilled in the art that almost any body fluid that can be drawn from a mammalian subject for isolation and modification of a particular component then safely reinjected into the subject are within the realm of the apparatus and method described herein. Such body fluids include, for example, cerebrospinal fluid, lymph fluid, amniotic fluid, synovial fluid, and the like, all of which can be withdrawn from the subject and modified using the apparatus of the present invention.

Referring to FIG. 1, the first stage of separation of a target component from a body fluid of a subject is carried out in a partitioning chamber (7) which houses some sort of separator or filtration means (9). The partitioning chamber can be any type of design suitable for dividing the body fluid into a manageable fraction containing target molecules of interest (filtrate) and the remainder of the fluid (retentate) which will remain untreated and be returned to the subject directly (without contacting the pathway travelled by the filtrate). The partitioning chamber (7) can be comprised of any suitable separator element for example, in the case of sampling blood from a subject, a separator element for removing cellular components from whole blood and allowing plasma containing the target antibody to pass through and be isolated on the filtrate side of the filtering means. The separator or filtering means (9) may suitably be a hollow fiber membrane, flat sheet membrane, membrane cassettes, rolled sheet membranes, and the like, and may be comprised of any material known in the art for the filtration of biological fluids, e.g., glass fiber filters, silicon, microporous membranes, polyethersulfone membranes, cellulose acetate membranes, etc. The partitioning chamber may also be a non-filter based component, such as a continuous centrifuge, which effectively isolates one component of the biological fluid, e.g., plasma from whole blood, for communication with the sequestering chamber via lines (8) and (8A).

The pore size of the filtering means may be any size or size range appropriate for selective passage of the target component. Preferably the pore diameter of the filtering means is from 0.05 μm to 1 μm and more preferably is less than 0.2 μm. Any type of separator designed to isolate the desired fraction of the withdrawn body fluid is suitable, as long as it performs the intended function of separating a targeted component from the withdrawn body fluid, e.g., separating plasma from cellular components of whole blood.

The partitioning chamber (7) may include one porous membrane or a series of porous membranes designed to allow a target molecule from the body fluid to flow through the membrane. The partitioning chamber may also be designed such that the membrane (9) is absent, allowing whole fluid to access the lines (8 and 8A) leading to the sequestering chamber. Alternatively, for some uses (for example, the capture of whole cells) line 1A may be connected directly to line 8 or to line 8A, and line 2A may be connected directly to line 8 or to line 8A. In the absence of a partitioning chamber, lines 8 and 8A may be the point of connection to the patient or fluid reservoir. These connection points may also be made from alternate components, including, but not limited to, luer fittings, rubber septums, hose-barbs or sealed ends. It is desirable, but not required, that these connection points be sterile and are able to be connected to the patient or fluid source without compromising sterility.

The separated body fluid fraction (e.g., blood plasma) on the filtrate side of the membrane is conducted via a conduit (8) through a 4-way selector valve (10) and to the sequestering chamber (12) which comprises a capture support for capturing and immobilizing the target component contained in the filtrate. The capture support can be comprised of any material suitable for the isolation or modification of the target. Various chromatographic supports are known in the art and may be used in the sequestering chamber. Suitable chromatographic supports include but are not limited to Blue Sepharose® (Sigma-Aldrich) for the capture of serum albumin, or Q Sepharose® Fast Flow (GE Health Care) for capture of nucleic acids from blood. For the immobilization of antibodies from a subject preparatory to labeling or modification, the capture support may be comprised of, for example, an immunosorbent material such as Protein A or Protein G, immobilized on an inert support of any of a number of materials known in the art. For example, the inert support may be comprised of silica, glass, N-hydroxysuccinimide (NHS)-activated Sepharose® beads, polyethersulfone (PES) membranes, etc. Linking the immunosorbent material to the inert support may be by any means known in the art. For example, the support material may be coated with an alkylaminosilane such as γ-aminopropyltriethoxysilane. The immunosorbent material, e.g., Protein A or Protein G, may then be linked to the amino-functional silanated support by means of a coupling reagent such as carbodiimide, glutaraldehyde, or an acid chloride.

Once the target molecule is bound to or immobilized on the capture support, the support can be contacted with a wash buffer such as PBS, illustrated in FIG. 1 as contained in a peripheral compartment (16) connected to the sequestering chamber (12). In one embodiment, the phosphate salts for a PBS buffer may be stored for use in a compartment (16) in powder form and can be reconstituted when needed by the addition of water-for-injection (WFI), illustrated in FIG. 1 as stored in a peripheral compartment (14). Following washing of the support, a label, e.g., $^{125}$I or other reagent may be introduced into the sequestering chamber (12) from a peripheral storage compartment or via an injection port (19) and directed via adjustment of 4-way selector valves (21 and 10) to the sequestering chamber (12) and the capture support to contact the immobilized target molecules. In one embodiment, the crosslinker or label is stored in compartment (26) and is activated upon hydration before introduction to the target component in the sequestering chamber (12).

As seen in the embodiment illustrated by FIG. 1, the inclusion of a plurality of independently operable 4-way selector valves (10, 11, 21, 22) are designed to direct the flow of materials (fluid, buffer, plasma, label, etc.) from several sources in the system, through the apparatus, by the manual or automated operation of a pair of syringe pumps (20, 23).

The fluid path within the apparatus is configured such that the only connections outside of the closed system are at the subject's circulatory system access points (1 and 2), which for blood sampling may be an arterial or venous puncture point (1) and a venous puncture point (2) of the subject. Peripheral compartments (e.g., 14, 16, 18, 24, 25, 26, 28, 33) and injection or sampling ports (5, 19, 31) also represent potential communication points with the environment outside of the closed circuit, and appropriate steps need to be taken to make sure that the flow path of the circuit is not opened or exposed to the environment at any of these points during operation of the apparatus if the closed circuit is to be maintained. The preferred design of the apparatus would be that most compartments (e.g., 16, 18, 24, 25, 26, 28, 33) will be intact and integral to the closed system prior to sterilization of the unit, and will either be empty or contain dried chemical components. The preferred design of the apparatus would also require the attachment of a reservoir of liquid (14), such as WFI, at a sterilizing filter (15). The maintenance of a closed system could also be ensured through alternative precautions, e.g., by filling, closing and sterilizing the peripheral supply compartments (e.g., 14, 16, 18, 24, 25, 26) prior to connection of the apparatus to a subject, by use of sterile filters on any system vents, and access ports, by use of appropriate valves (e.g., 29, 30) or airtight, watertight septums. The maintenance of a closed system may also be maintained by assembling the compartments, or the capture support/sequestering chamber, aseptically or by a sterile connector or by using a Sterile Connection Device (SCD).

Fluid flow within the circuit may be continuous or intermittent, or may be continuous in part of the system (for instance on the retentate side) and intermittent in another part (on the filtrate side). One or both of the connection points (1 and 2) to the subject may be closed or removed during operation of the apparatus. Blood can be collected and immediately applied to the partitioning chamber by any means, with or without anticoagulants. Fluid does not need to be in circulation for the device to operate.

As illustrated in FIG. 1, the flow of fluids through the apparatus is controlled manually or automatically via two syringe pumps (20, 23). However, it will be understood that the apparatus can be designed with additional syringe pumps as necessary, or that one or more of the syringe pumps can be substituted with any suitable means (manual or automated) for conducting fluids etc. through the apparatus, e.g., by the addition to the apparatus of one or more peristaltic pumps, piston pumps, diaphragm pumps, by gravity, or by reliance on the systemic pressure (e.g., blood pressure) of the subject. For example, a suitable position for a peristaltic pump could be along line (8) or line (1A), although other potential sites may also be functional.

Figure 2:
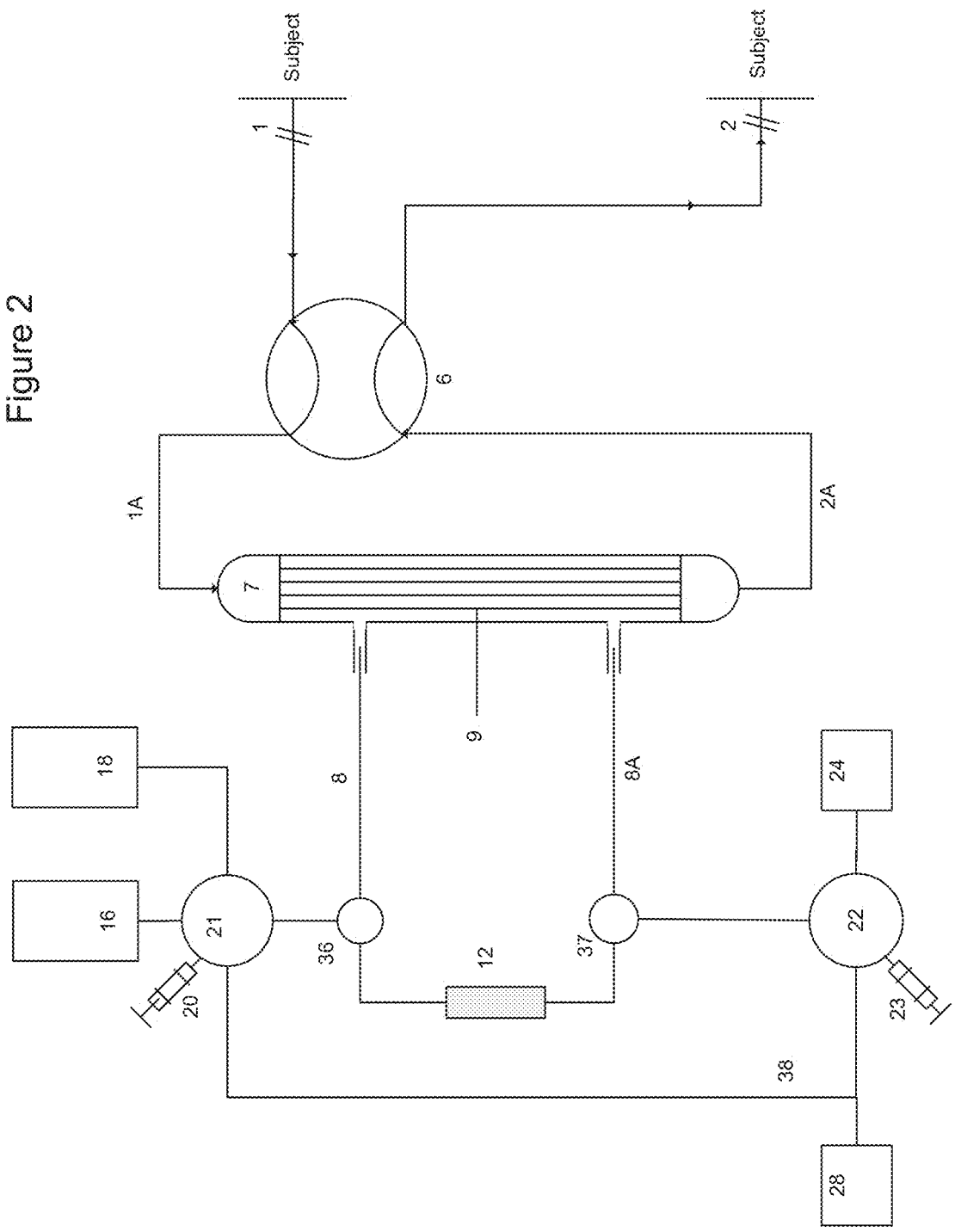
FIG. 2 is a schematic diagram showing an alternative embodiment of the apparatus of the present invention, utilizing a pair of three-way stopcock valves (36 and 37) and a T-connector (38), the operation of which is described in Example 1, infra.
Figure 3:
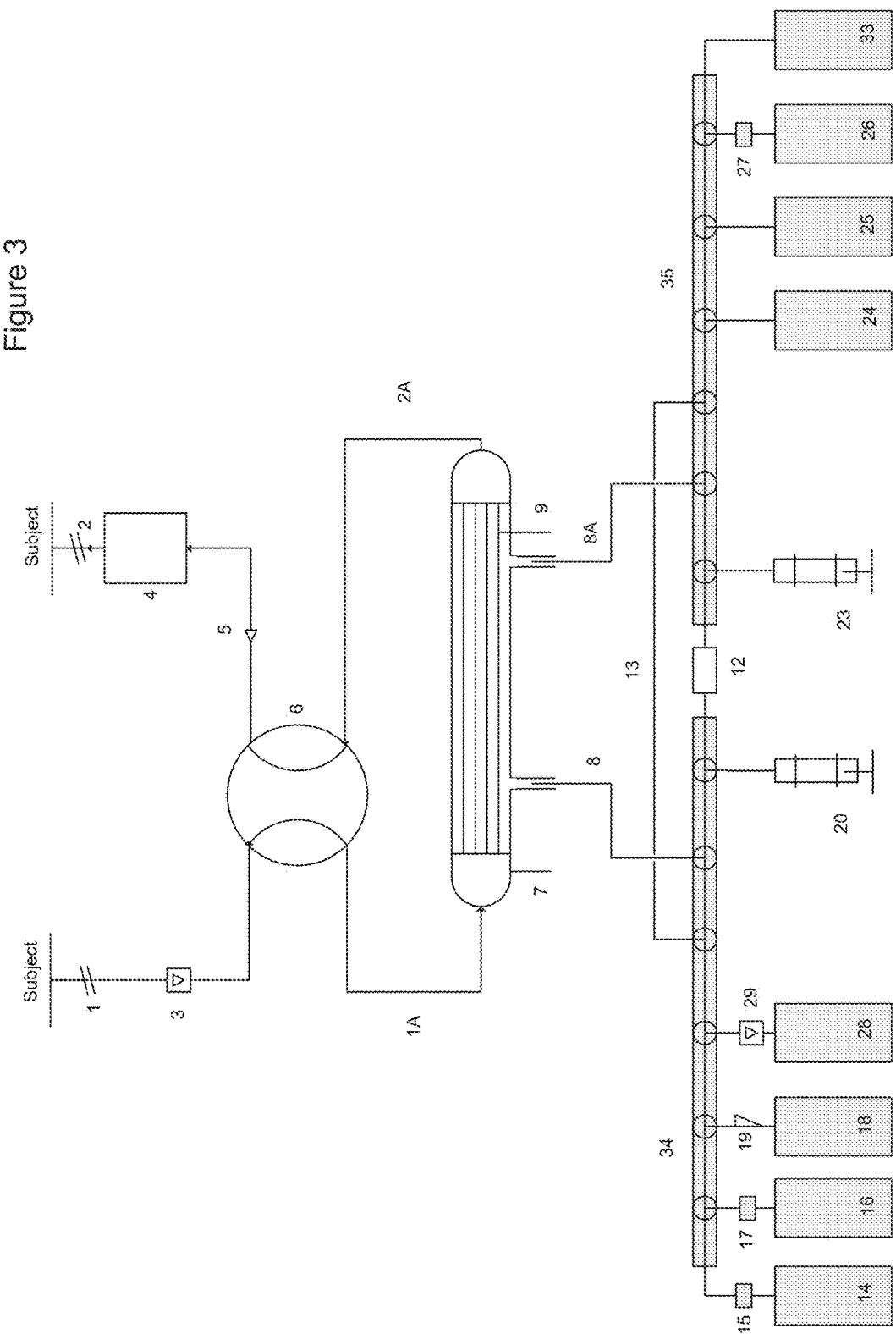
FIG. 3 is a schematic diagram of an apparatus according to the invention showing an alternative embodiment utilizing a pair of linear manifolds (34 and 35) for regulating fluid flow within the closed circuit of the system.
Figure 4:
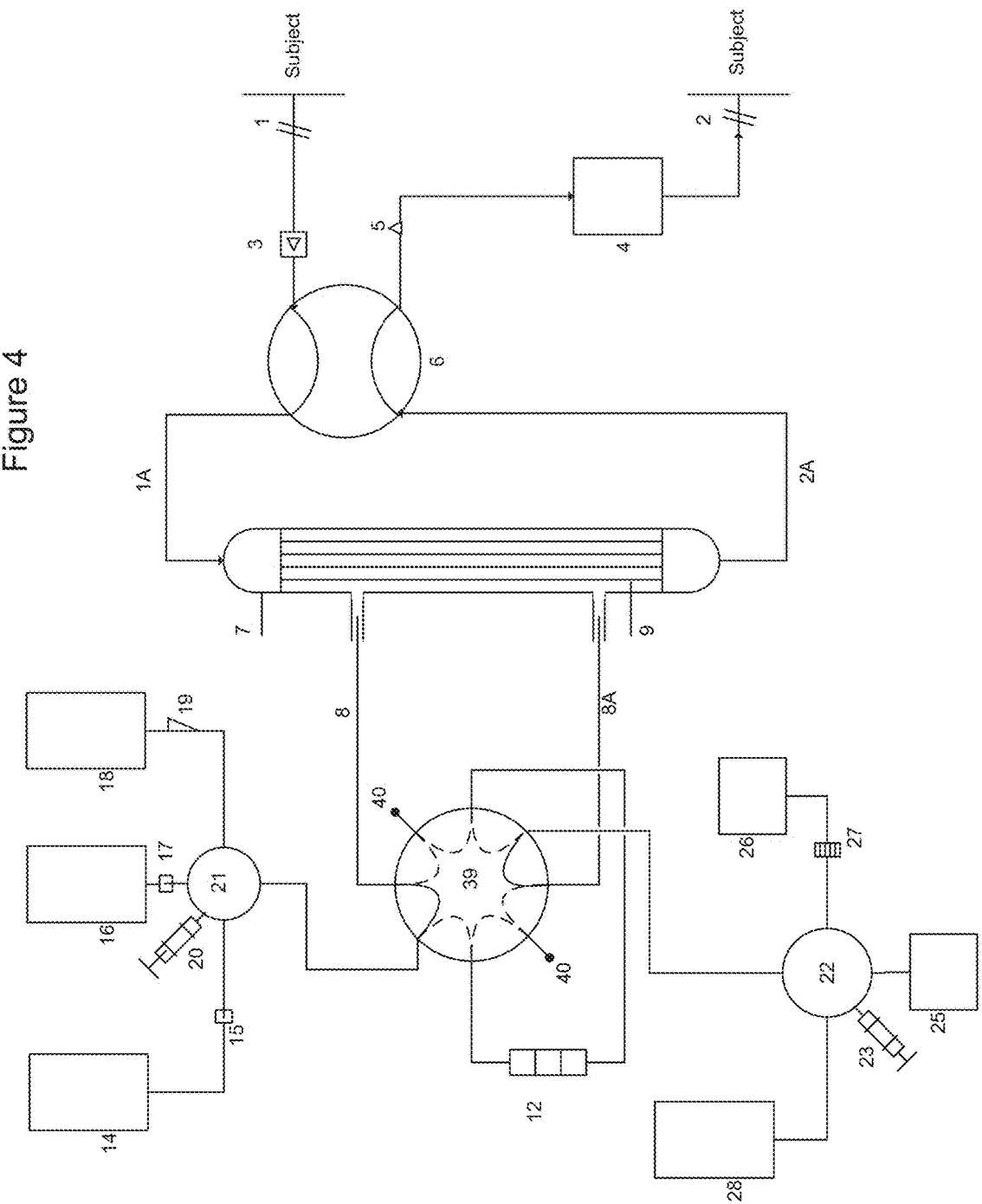
FIG. 4 is a schematic diagram of an alternative embodiment of the apparatus of the present invention utilizing a single multiport valve (39) to select various flow channels, with plugs (40) blocking the unused channels.

The 4-way selector valves (10, 11, 21, 22) could alternatively be replaced by two 6-position manifolds (34, 35 in FIG. 3), a series of stopcocks (36, 37 in FIG. 2), 8-way 2-channel valves (39 in FIG. 4), or some other alternative configuration (See FIGS. 2, 3, 4).

Also, any of the illustrated peripheral reservoirs and compartments (14, 16, 18, 24, 25, 26, 28, 33) can be substituted with removable "I.V."-type bags or other containers, such as syringes, containing any of the necessary solutions, WFI, chemicals, etc. These compartments may also be of a rigid structure, which may be fitted with a vent filter, preferably 0.2 micron, to prevent the formation of positive or negative pressure in the compartment.

Referring to FIG. 3, the injection port (19) can be modified to accept, for example, a syringe containing the label, drug, etc., for injection into the apparatus, or it could be a drip chamber or a valve connection to a separate compartment containing a component of the modification procedure. Compartments (25) and (26) could both contain dry chemical for neutralization, enabling the device to be used twice, with two separate chemical modifiers injected at port (19), both of which are bound to separate but identical IgG pools, and sequentially delivered to the patient. Alternatively, non-covalent modifiers could be present in compartments (18), (24), (25), and/or (26). An activated filter (27) may optionally be present to remove contaminants or by-products of the chemical modification and subsequent elution. Filter (27) could also be an affinity membrane or matrix functionalized with, for example, IgM or other affinity molecule. Filter (27) could also be an alternative or additional capture support.

A switchable bypass (32) may be plumbed between two elution collection chambers (e.g., at 25 and 26), allowing for direct transfer of eluted target molecule between the two chambers without passing through a switching valve (22) or in-line filter (27). Alternatively, the bypass may contain an in-line filter which may be designed to have binding characteristics which favor the immobilization of the target molecule or a contaminating or co-eluting molecule.

Within the sequestering chamber (12) any modification reaction can be carried out in isolation from the general circulation of body fluid from a subject entering the system via the inlet (1). For example, the targeted component isolated in the sequestering chamber can be modified by the addition of homobifunctional or heterobifunctional cross-linkers such as, but not limited to sulfo-NHS, sulfo-SMCC, hydrazide (which couples to carbohydrates), EDC, SPDP (immunotoxin labeling), Traut's reagent, SASD, SFAD, or LCABH (photoreactive to carbohydrates). The targeted component can be modified by the addition of radioactive tags and probes, for example, covalent modification of Tyrosine, Histidine and phenolic rings by treatment with SHPP (Bolton and Hunter reagent), chloramine-T, or lactoperoxidase, then Iodine-125, covalent modification of disulfides, with or without reduction techniques (2-iminothiolane, SATA, PDPH) using Tc-99m, and bifunctional chelating agents (BCA) such as DTPA, DOTA, NOTA, TETA, DFA. Antibodies and antibody fragments are especially suitable for in-circuit modification according to this invention and may be usefully labeled with a number of specific radionuclides for use in clinical diagnosis or immunotherapy. These radionuclides include, but are not limited to, $^{131}$I, $^{125}$I, $^{123}$I, $^{99m}$Tc, $^{67}$Ga, and $^{111}$In. Other types of modification of the target components include the use of such reagents as N-glycanase (for deglycosylation), sialidase (for deglycosylation), Yttrium-90 (cytotoxic therapy), $^{131}$I (cytotoxic therapy), conjugation partners such as immunotoxins (therapeutic) such as ricin A, abrin, gelonin, PAPs, ribosome inactivators (RIPs), taxol, and calicheamicin, or conjugation partners such as immunomodulators such as interleukins, cytokines or chemokines.

The coupling of labels or therapeutics, or other modifications of the target component, can be enhanced by the introduction of temperature or UV light of a specific or general wavelength at the site within the apparatus where the labeling reaction is taking place.

The coupling of labels or therapeutics, or other modifications of the target component, may or may not involve covalent reactions, for example the therapeutic entity may be a monoclonal antibody that binds to the targeted component, or it may be a radioactive divalent cation that locates to a chelating site on the targeted component.

From the foregoing description, it can be seen that the apparatus of the present invention is particularly suited for use in nuclear medicine. Nuclear medicine involves the use of radioactive substances for both diagnosis and treatment of disease, and has useful applications in several medical fields, notably oncology, neurology, and cardiology. Methods for evaluation or diagnosis of disease typically involve the administration of a relatively short-lived radioactive isotope to the patient, coupled with a method to detect the distribution of the isotope in vivo. Detection methods such as scintigraphy, gamma cameras, single-photon emission computed tomography (SPECT), computed tomography (CT) and positron emission tomography (PET) allow for the collection of two-dimensional and three-dimensional images from the patient. Data from these scanning methods can be used to evaluate a physiological condition or disease.

For example, positron emission tomography (PET) has been used to assess the rate of metabolic utilization of glucose in tissues. A short-lived positron emitting isotope, such as $^{18}F$, is incorporated into the glucose molecule prior to administration to the patient. The radiolabeled carbohydrate carries the incorporated detectable isotope to sites of high metabolic activity in the patient. Images of the distribution of metabolic activity throughout the body can highlight rapidly growing tissue (such as a tumor), metastasis of cancer cells, or sites of infection.

Radioisotopes can be administered to a patient by a number of vehicles, including proteins, to target the diagnostic reagent to a specific site of interest, or to evaluate the distribution of the vehicle in the patient. Immunoglobulins, especially IgG antibodies, exhibit high specificity and affinity toward their complementary target molecules (antigens), making them very useful as vehicles for targeting radioisotopes or other effector substances to particular sites in vivo, for diagnostic or therapeutic purposes. For example, considerable progress has been achieved during the last two decades in the use of radiolabeled tumor-selective monoclonal antibodies in the diagnosis and treatment of cancer. The concept of localizing a cytotoxic radionuclide at the site of the cancer cell is an important supplement to conventional forms of radiotherapy. The proximal contact between a radioactive antibody conjugate and a target cancer cell enables the absorbed radiation dose to be concentrated at the site of abnormality with minimal injury to the normal surrounding cells and tissues. Differential binding of radiolabeled antibodies to cancer cells can also be used for imaging and localizing tumors. In order to image tumors with antibodies, the antibodies must target the antigens on the tumor cell that differentiate it, either qualitatively or quantitatively, from antigens on surrounding normal cells. Thus, antibodies can be used to image a particular cell type if the cell expresses a unique antigen recognized by the antibody or if the cell expresses a detectably higher quantity of surface antigens than normal cells, permitting detection and imaging to be made on the basis of the density of labeled antigens binding to target cells. Ideally, the targeted antigens are unique to tumor cells (i.e., not found in any normal tissue in any amount).

The use of monoclonal antibody/radionuclide conjugates for the diagnosis and treatment of cancer has become well established. See, e.g., Pietersz et al., *Immunol. Cell Biol.*, 65: 111-125 (1987).) Suitable radionuclides for these uses include $^{90}Y$, $^{188}Re$, $^{186}Re$, $^{199}Au$, and $^{67}Cu$. $^{131}I$ has also been used. With the exception of $^{131}I$, all the methods currently used to conjugate these radiometals to antibodies involve the use of chelating groups chemically attached to the antibody.

Monoclonal antibodies may be utilized to deliver a therapeutic molecule, or an imaging agent, to a targeted site in vivo. For example, Ibritumomab tiuxetan (Zevalin®; Spectrum Pharmaceuticals, Inc., Irvine, Calif.) is a radionuclide-conjugated monoclonal antibody which recognizes the cell surface antigen CD20. CD20 is a marker on neoplastic B cells and is found on B cell lymphomas, in hairy cell leukemia, and in chronic lymphocytic leukemia. The ibritumomab monoclonal antibody, conjugated to a proprietary chelator, is useful as a carrier to distribute both Indium-111 (an imaging agent) and, separately, Yttrium-90 (a therapeutic agent) to tissues in vivo that express CD20 surface antigens. Thus, ibritumomab tiuxetan is used as both a diagnostic reagent and a targeted therapeutic. When coupled to Indium-111, the antibody, after injection into a patient, can be detected and the distribution of radiolabeled monoclonal antibody can be evaluated, following whole-body detection using a planar x-ray camera. The specific recognition sites, and the quantitative assessment of the amount of conjugated antibody at these sites and other locations in vivo, may then be assessed by a radiologist to determine if the patient is a suitable candidate for CD20-targeted therapy. If so, the conjugated monoclonal is coupled to Yttruim-90 for site-directed delivery of the cytotoxic radiation.

By following the description herein, an apparatus may be designed to produce, in a closed circuit and while connected to a patient, diagnostic nuclear imaging reagents and/or therapeutic conjugates having a binding protein (e.g., an antibody) from the patient linked to a radioactive therapeutic agent or a cytotoxic agent, for reintroduction into a patient, without extracorporeal handling or contamination, for diagnostic or therapeutic purposes.

The device can be used to readminister a previously retained component at a later date, to monitor progress of the disease or the patient's response to the disease, or to treat a recurrence of the disease, including sites of metastasis.

Setup for Operation

Referring to FIG. 1, the configuration of the 4-way selector valves (21) and (22) are such that the syringe pumps (20) and (23) are connected at the bottom face of the valve (along the "z" axis), and are always in connection to the fluid path. By rotating valves (21) and (22) in 90 degree increments, the syringe will selectively be in contact with one of the four pathways associated with the valve. For example, when valve (21) is set to 270 degrees, the syringe (20) will be in fluid contact with WFI in compartment (14). When valve (21) is set to 0 degrees, the syringe (20) will be in fluid contact with PBS in compartment (16). When valve (21) is set to 180 degrees the syringe (20) will be connected at the bottom face of the 4-way selector valve (10) (along the "z" axis). Valve (10) is connected to four pathways and places the sequestering chamber (12) in contact with valve (21) when the valve (10) is at 180 degrees. Similarly, when valve (22) is set to 0 degrees the syringe (23) will be connected at the bottom face of the 4-way selector valve (11) (along the "z" axis). Valve (11) is connected to four pathways and places the sequestering chamber (12) in contact with valve (22) when the valve (11) is set at 0 degrees.

Prior to use and operation, the entire apparatus may advantageously be UV sterilized and packaged accordingly until needed. The apparatus may also be sterilized, in whole or in part, by any suitable method known in art, and may be assembled using sterile or aseptic technique, if required, before use. Preferably, prior to use, the apparatus is "primed" by filling all tubing channels, chambers and compartments to facilitate the flow of fluid, blood, buffer, etc., throughout. The apparatus may be designed such that compartment (14) may be filled by the operator. The apparatus may be designed such that compartment (14) is not part of the completed sterile apparatus and is instead an external reservoir attached prior to use. To prime the apparatus, the operator (technician, physician, etc.) may for example attach a container of sterile Water-For-Injection (WFI) (14) at the 0.2 µm syringe port (15) which is in fluid connection with the entire system via a 4-way selector valve (21). By setting the 4-way selector valve (21) to 270 degrees, WFI is withdrawn from the compartment (14) into syringe pump (20) by operation of the syringe. By then rotating valve (21) to the 180 degree position and rotating 4-way selector valve (10), which is in fluid communication with 4-way selector valve (21), to the 270 degree position, air can be systematically expelled through the check valve (29) and collected in the attached waste compartment (28). Once the fluid connection lines and syringe (20) have been primed, valve (21) can be rotated to the 90 degree position and WFI in the filled syringe (20) can be directed into compartment (18) in a measured volume to hydrate the dry chemical (for example, carbonate buffer) contained within. Mixing of the WFI and chemical can be enhanced by withdrawing and expelling the solution in compartment (18) using syringe (20) with valve (21) positioned at 90 degrees. By rotating valve (21) to 180 degrees, valve (10) to 0 degrees, valve (11) to 180 degrees and valve (22) to 0 degrees, WFI can be transferred to syringe (23) via bypass line (13). Bypass line (13) can be of any volume and can also serve as a holding reservoir. Bypass line (13) may be replaced with another capture (affinity) support and could alternatively be used for capture prior to or immediately following capture at the sequestering chamber (12).

It will be readily understood that by replacing valves (10) and (11) with 6-way or 8-way selector valves, multiple capture supports of the same or different binding chemistry could be plumbed between the valves, essentially creating a number of separate parallel sequestering chambers within a single apparatus. Multiple sequestering chambers of the same or different binding chemistry may also be plumbed in series.

Air can then be expelled from syringe (23) by rotating valve (11) to 270 degrees and expelling through 3-way valve (30) and into waste compartment (33). Once the lines have been primed and syringe (23) is filled, e.g., with WFI, dry elution buffer components (such as sodium acetate) contained in compartment (24) can be hydrated and mixed, i.e., by setting 4-way selector valve (22) to 270 degrees and operating syringe (23). Alternatively, the elution buffer can already be in solution when added to compartment (24). Phosphate-buffered saline (PBS) (16) can be attached to the apparatus at filter (17) which is in fluid communication with 4-way selector valve (21). The fluid communication may optionally include a sterile filter (17). By rotating selector valve (21) to 0 degrees, PBS may be drawn into syringe (20). By rotating valve (21) to 180 degrees, and rotating valve (10) to 180 degrees, the PBS can be used to rinse the capture support of the sequestering chamber (12). It will be appreciated by those skilled in the art that any number of capture supports or reactive surfaces can be used in sequestering chamber (12) depending on the desired target component for isolation from the fluid withdrawn from the subject and the desired modification of the target to be performed. Similarly the filtrate side of the separator (9) of the partitioning chamber (7) can be flushed with PBS by turning valves (10) and (11) to 90 degrees, valve (21) to 180 degrees and valve (22) to 0 degrees. The primed apparatus is ready to be attached to the patient's circulatory system at inlet connection (1) (for the purpose of this example, an artery) and outlet connection (2) (for the purpose of this example, a vein) as illustrated in FIG. 1.

Operation for Isolation and Immobilization of IgG from a Patient

By way of illustration, the operation of a system such as diagrammed in FIG. 1 for the isolation and labeling of IgG from a patient will be described. It will be understood that the steps described below are carried out by the selective adjustment of the 4-way selector valves (10, 11, 21, 22) and selective operation of the syringes (20, 23) of the apparatus.

An arterial catheter (1) is attached to the patient to access the patient's blood supply. Blood is drawn through the check valve (3), and through safety valve (6). If at any time during the process complications arise from the separator (9) or by any of the mechanics and components on the filtrate side of the separator, safety valve (6) can be turned 90 degrees to conduct flow from the inlet (1) directly to the outlet (2) and thereby isolate the patient from any components of the circuit that are downstream of the safety valve (6), until the procedure is either brought under control or is aborted. In this aspect, blood withdrawn from the patient via inlet catheter (1) is directly reinjected back into the patient via outlet catheter (2).

The withdrawn blood conducted through the safety valve (6) along inlet line (1A) then enters the partitioning chamber (7). Separation of whole blood by passage of plasma through the separator filter (9) creates a filtrate side and a retentate side to the circuit. Differential pressure that exists at different points of the circulatory system of the patient can provide positive flow through the plasma separator (9), however, an active pumping system, for example, a peristaltic pump, can be incorporated to assist this process. With extracorporeal flow of blood being maintained through the retentate side of the separator (9), valve (10) can be rotated to 90 degrees to allow syringe (20) to draw plasma proteins through line (8) that have diffused across the filtering membrane (9) into the filtrate side of the system. If displacement of the withdrawn filtrate is not compensated for by expelling replacement buffer from the filled syringe (23), then plasma will be drawn across the filtering membrane (9) by negative pressure. By rotating valve (21) and valve (10) to 180 degrees, and valve (11) and valve (22) to 0 degrees, syringe (20) can then deliver the drawn plasma proteins across the affinity support within sequestering chamber (12), allowing plasma IgG to bind to the capture support, e.g., a protein A matrix. Flowthrough plasma that is now at least partially depleted of IgG is collected in syringe (23). This depleted plasma can be returned to the patient by rotating valve (11) to 90 degrees and conducting flow back to the partitioning chamber (7) via return line (8A). Alternatively, the volume of depleted plasma can be used to compensate for the withdrawn filtrate as described above. This process can be repeated several times to effectively process enough plasma to bind an effective amount of IgG to the affinity capture support of the sequestering chamber (12).

Alternatively, to remove excess plasma from the affinity capture support in sequestering chamber (12), syringe (20) can be filled with PBS from compartment (16) by rotating valve (21) to 0 degrees. The valve configuration can then be restored as described above to allow filled syringe (20) to deliver PBS across the affinity capture support of the sequestering chamber (12), effectively washing away the majority of the excess plasma proteins other than captured IgG, which is bound to the support. PBS wash that is collected in syringe (23) can be expelled to the waste compartment (33) by rotating valve (11) to 270 degrees.

Labeling the IgG Immobilized on the Capture Support

Once the affinity capture support has been washed with PBS from compartment (16), carbonate buffer from compartment (18) can be withdrawn to syringe (20) and used to flush the support. Once the support has been flushed with carbonate buffer, a specific labeling reagent (for example, Bolton and Hunter reagent (Thermo Scientific, catalogue #27710) can be introduced into the flowpath at injection port (19). The reagent can be cycled back and forth across the affinity support which contains bound IgG, by the action of syringes (20) and (23) with valves (21) and (10) set at 180 degrees and valves (11) and (22) set at 0 degrees. After labeling of the IgG is complete, the column can be washed to waste (33) using either PBS (16), WFI (14) or carbonate buffer (18). Radioactive isotopes may be similarly incorporated.

Elution of Labeled IgG from the Capture Support and Return to the Patient

Elution buffer stored in a peripheral supply compartment (24) can be drawn by syringe (23) and then washed across the affinity support to syringe (20) in a similar manner to the labeling reagent, above. The eluted labeled IgG product can be optionally neutralized by delivery and mixing into a neutralizing compartment (25) which may advantageously contain a dry chemical buffer for maintaining a physiological pH, such as HEPES. The eluted product can be delivered into holding compartment (26) either before or after neutralization. As diagrammed here, this transfer will entail passing the material through a filter (27) which may be modified according to any of a number of known chemistries (for example, cation exchange groups) which can be used to deplete the eluted labeled product of any unwanted byproduct, such as aggregates or free reagents. Any number of such filters, in any combination of modifications or functionalities, can be incorporated at various locations within the device. Finally the eluted labeled product is drawn into syringe (23) from either compartment (25) or (26), and then expelled to the partitioning chamber (7) by rotating valve (22) to 0 degrees and valve (11) to 90 degrees. Transfer of labeled product across the separator membrane (9) can occur by osmosis or by positive pressure exerted by operation of syringe pump (23), which can be filled repeatedly with PBS or other solutions delivered from storage compartments (14, 16, 18). Likewise, positive pressure can be exerted through the action of syringe pump (20). Labeled IgG will then be mixed with whole blood of the retentate and reinjected into the patient via outlet catheter (2). The outlet line (2A) connecting the partitioning chamber (7) with the outlet catheter (2) may optionally include an injection port (5) for addition of a solution, e.g., an anticoagulant, and a drip chamber (4) to control the rate of flow of fluid and prevent the flow of air bubbles back into the patient. The drip chamber (4) may alternatively be positioned in the pathway (1) either upstream or downstream of the check valve (3). Note that if a sample of the eluted labeled IgG or plasma flowthrough is desired, the three-way valve (30) can be turned to divert liquid from syringe (23) for collection and removal at the sample port (31).

FIGS. 2, 3, and 4 show alternative embodiments of the closed circuit of the present invention. The numbering of the components in FIGS. 2, 3, and 4 is as described above for FIG. 1.

EXAMPLES

Example 1

The method of the present invention was carried out using a novel apparatus constructed according to the diagram of FIG. 2.

Fresh whole bovine blood was collected and immediately mixed 9:1 (v/v) with ACD anticoagulant (0.73M trisodium citrate, 0.35M citric acid, 0.10M glucose, pH 5), then stored at 2-8° C. for 1 week. Blood was resuspended and passed through a coarse nylon filter prior to use. The apparatus was assembled as shown in FIG. 2, using a new MidiKos ME/0.2 micron 105 cm$^2$ hollow fiber membrane filter (Spectrum #X22M-300-02N) housed in tubular plastic casing as the partitioning chamber (7), and a 1 mL Protein A HiTrap™ column (GE Healthcare #17-5079-02) in the sequestering chamber (12). Syringes (5 mL volume) were attached at positions (20) and (23). A T-connection (38) was run from one of the ports at both valve (21) and valve (22) which was plumbed to a waste vessel (28). Two three-way stopcocks were positioned at (36) and (37), allowing access at valves (21) and (22) to either the Protein A affinity column (12) or the hollow fiber filter device (7). A reservoir of PBS (Sigma kit PBS-1) was attached at position (16). A reservoir of labeling buffer (0.2M sodium carbonate, pH 9.34) was attached at position (18). A syringe filled with elution buffer (0.1M acetic acid) was attached at position (24). The syringe pumps (20) and (23) were used to flush the lines with 1 mL each from compartment (18) and compartment (24), then were used to flush PBS from compartment (16) to displace all air in the remaining lines of the device including the Protein A column (12) and the filtrate side of the hollow fiber membrane cassette (7). The plunger of the syringe (20) was fully depressed and contained no volume. The syringe (23) initially contained 5 mL of PBS.

Whole blood (375 mL total) was then flushed from inlet 1, through the safety valve (6), through the retentate side of the partitioning chamber (7), back into the safety valve (6) and finally into a blood collection vessel at outlet (2). This flow was maintained at approximately 8 mL/min. by gravity using an 18-inch height differential from inlet (1) to outlet (2). Liquid on the filtrate side of the hollow fiber membrane (9) was then drawn into the syringe (20), while an equivalent volume of PBS was delivered at approximately the same flow rate to the filtrate side of the membrane by syringe (23). Valves (36) and (37) were then repositioned to allow the delivery of the collected filtrate by the syringe (20) to the Protein A column (12) at approximately 2 mL/min., with collection of the effluent at syringe (23). The valves (36 and 37) were then positioned to select the filtrate side of the hollow fiber filter (9), and liquid was again drawn into the syringe (20), with displacement by the effluent that had been collected in syringe (23). Similarly, this filtrate was then re-routed to flow over the Protein A column (12) at 2 mL/min., with effluent collection at syringe (23). This process was repeated until a total of 60 mL of filtrate had been passed over the column over a time span of approximately 60 minutes. Aliquots of unprocessed and processed whole blood were retained for assays.

Syringe (20) was flushed four times with PBS from compartment (16), then used to wash the column (12) with three aliquots of PBS of 5 mL each, then with three aliquots of labeling buffer from compartment (18) of 5 mL each. Effluent from these steps was collected by syringe (23), then discarded to a waste compartment (28).

To mimic the addition of a label being introduced at an injection port (or equivalent), a vial of EZ-link Plus Activated Peroxidase (Thermo Scientific, Pierce Chemical, cat. #31487) was completely dissolved in 2 mL of labeling buffer and attached at position (18), after removal of 0.1 mL for assays. 1.9 mL of dissolved label was pulled into syringe (20), then loaded onto the Protein A column (12) at 1 mL/min., followed by a chase of 1 mL of labeling buffer. The effluent from these steps, containing unbound label, was collected in syringe (23). This material was then cycled back and forth through the column (12), from syringe (23) to syringe (20) and back, for a total of 9 passes at 1 mL/min. The depleted label was collected for assay purposes, along with the first of three washes of the column (12) using 5 mL of labeling buffer each time. The column (12) was then eluted by flow from syringe pump (23) to syringe pump (20) at 1 mL/min using the elution buffer conducted from a reservoir at compartment (24). Eluent was passed back over the column (12) from syringe (20) to syringe (23) and stored in compartment (24), along with a 3 mL labeling buffer chase from compartment (18) to neutralize the solution, for a total of 8 mL eluent volume collected in (24). The column (12) was subsequently washed by three labeling buffer washes (5 mL each) and three PBS washes (5 mL each), with collection at waste compartment (28).

The reservoir of filtered blood collected at outlet (2) was resuspended and returned to the feed reservoir at inlet (1). Following this, 6 mL of the neutralized eluted product in compartment (24) was directed to the filtrate side of the hollow fiber membrane (9) in the partitioning chamber (7) by the action of the syringe (23), without any displacement from the opposite syringe (20), effectively driving the volume across the hollow fiber membrane (9) and into the flowpath of the whole blood on the retentate side of the membrane. This was followed by a total of 5 chases of 5 mL each PBS, two chases from syringe (23) and three chases from syringe (20). The remaining 2 mL of neutralized elution material at position (24) was removed for assays. The total volume of whole blood from the feed and retentate ports was mixed together for a total of 390 mL, with approximately 15 mL lost due to sampling and holdup in the device.

Protein quantitation of the amount of bound and eluted target antibody, and of the amount of label incorporated during the reaction, was by colorimetric Bradford Assay using Coomassie Plus reagent (Pierce Chemical, cat. #1856210) measured at 595 nm on a spectrophotometer. Dilutions of albumin (Pierce Chemical, cat. #23209) in dilution buffer (5 parts elution buffer plus 3 parts labeling buffer) were mixed 1 part to 20 parts reagent, then read on the spectrophotometer after 5 minutes to create a standard curve. These readings were compared to similarly-prepared retains of HRP-label, depleted HRP label, and eluted protein from the labeling study. Results indicated that approximately 3.2 mg of antibody was recovered from the Protein A column sequestering chamber.

Quantitation of HRP activity for the eluted protein and of HRP activity recovered in the whole blood following the return of 6 mL of the eluted protein was by colorimetric assay using Slow TMB 1-step (Pierce Chemical, cat. #34024) measured at 655 nm on a spectrophotometer. Dilutions of a retain of the solubilized EZ-link Plus Activated Peroxidase (Pierce Chemical, cat. #31487) in dilution buffer were mixed 1 part to 10,000 parts TMB reagent, and read on the spectrophotometer after 5 minutes of development to obtain a standard curve of HRP activity. These readings were compared to similarly-prepared retains of depleted HRP label, labeled eluted protein, plasma prior to introduction of eluted protein, and plasma following the return of the labeled protein (all at various dilutions to accommodate for colorimetric activity of the retains). Results indicated that approximately 3% of the available HRP label was incorporated into the eluted protein, and approximately 70% of the available labeled eluted protein (after retains) was returned to the "circulating" whole blood at the completion of the procedure.

Identification of the bound, labeled and eluted protein was by SDS-PAGE run on 4-15% Ready Gels (BioRad, cat. #161-1158) in Tris/Glycine/SDS buffer (BioRad, cat. #161-0732) and 2× Laemmli Sample buffer (BioRad, cat. #161-0737) then stained with Bio-Safe Coomassie (BioRad, cat. #161-0786). Depleted plasma (following the binding procedure but prior to the return of the labeled protein), a retain of the prepared HRP label, labeled purified protein, and bovine IgG control (Sigma 15506), along with a reduced sample (heated for 5 min. with the addition of 5% beta-mercaptoethanol, BioRad, cat. #161-0710) of the labeled purified protein and the bovine IgG control, were all run on the same 4-15% gel at 100V for 3 minutes and 150V for 47 minutes. After the run was completed, the gel was rinsed in water, stained for 6 hours and then washed twice in water. When compared to Precision Plus protein standards (Bio-Rad, cat. #161-0374) that were also run on the gel, it was apparent that both the labeled purified protein and the bovine IgG control contained major bands at just over 150 kDa, which both ran as two separate bands at 50 kDa and 25 kDa under reducing conditions, indicating that the purified protein was IgG.

In summary, 3.2 mg of polyclonal immunoglobulins were captured on the affinity support in the sequestering chamber. The target immunoglobulins were then labeled by the covalent attachment of n-hydroxysuccinimide-conjugated horseradish peroxidase (NHS-HRP). Excess reagents were washed away prior to elution of the labeled immunoglobulins. Results confirmed that approximately 3% of the NHS-HRP reagent was covalently attached to the captured immunoglobulins. The eluted material was then returned to the extracorporeal circuit across the same membrane of the partitioning chamber. The colorimetric enzyme assay was used to determine that approximately 70% of the labeled IgG was successfully administered back into the recirculating whole blood.

As will be appreciated by those skilled in the art, the novel apparatus described herein possesses immeasurable potential to treat a limitless number of disease states accessible to any mammalian circulatory system (blood, amniotic, spinal or lymphatic). The device can make use of an existing physiological response or condition by imparting enhanced or novel properties to a targeted component in circulation. By choosing the selectivity of the capture support (to immobilize any particular component), and coupling a label or other compound to the component, a new diagnostic visualization agent or therapeutic agent can be manufactured in situ, then introduced into the subject for diagnostic imaging or targeted therapy. Modification of the component by chemical means may also impart improved or novel characteristics. Furthermore, by the coupling of therapeutic compounds to a targeted component, a wide variety of therapeutic treatments can be applied to the patient. The effectiveness of the therapeutic compound may be enhanced by the physiological properties of the targeted component, and may include site-specific targeting, increased solubility, and improved pharmacokinetic properties. Therapeutic treatments can also be directly applied in the absence of diagnostic imaging to target elusive cells or tissues that fall below the limit of detection, for example, metastatic cancer cells or recently contracted infectious agents such as anthrax. The effectiveness of the targeted therapy is determined partially by the chemical and physiological makeup of the patient. The patient can be any mammal with a circulatory system capable of accommodating the volumes required by the device.

The secondary (adaptive) immune response involves the activation of a number of the components of the immune system, including lymphocytes, cytokines, and the production of immunoglobulins. These components mount a coordinated attack on foreign molecules, cells or tissues (such as a viral or bacterial infection), or on mutated and malfunctioning innate molecules, cells or tissues (such as malignant tumor cells). The immunoglobulin component of the adaptive immune response is polyclonal and is composed of numerous (monoclonal) antibodies in varying proportions. Each population of (monoclonal) antibody is derived from a unique cellular source and recognizes a unique feature of the targeted cell or tissue associated with a disease. The secondary immune response may sometimes be ineffective at neutralizing and eliminating the disease state. In these cases, polyclonal antibodies which specifically recognize the disease may still be present, and could function effectively to target a radioisotope for disease detection, assessment or therapy. Antibodies could also be coupled to an immunomodulator, to induce, enhance or suppress an immune response. Lymphocytes produced by the immune system could likewise be manipulated and utilized.

The immunoglobulin component of the adaptive immune response may be composed of autoantibodies, or polyclonal antibodies active against a tissue constituent of the individual producing it. U.S. Pat. No. 5,870,033 (Torchilin et al.) describes use of purified autoantibodies (obtained from autoimmune patients) for tumor therapy; U.S. Pat. No. 7,799,327 (Smith et al.) describes use of autoantibodies as a carrier for tumor imaging and cancer therapy. As can be seen from the foregoing example and the detailed description above, the apparatus of the present invention provides a means for in situ extracorporeal preparation of imaging agents and self-targeting therapeutic agents in a closed circuit, using a patient's own immunoglobulins as carriers and without handling the proteins or exposing them to exogenous contamination before introduction into the patient. By following the methods and teachings set forth herein, a wide variety of new applications for body fluid treatment and development of novel therapeutics and diagnostics has been made available.

Preferred embodiments of this invention are described herein, including the best mode known to the inventor for carrying out the invention. Variations of those preferred embodiments may become apparent to those skilled in the art upon reading the foregoing description. The inventor expects skilled artisans to employ such variations as appropriate, and the inventor intends for the invention to be practiced otherwise than as specifically described herein for illustrative purposes. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

What is claimed is:

1. An extracorporeal closed-circuit apparatus comprising:
   (a) an inlet configured to access the body fluid of a mammalian subject;
   (b) a sequestering chamber connected to said inlet which allows passage of said body fluid into said sequestering chamber, said sequestering chamber comprising a capture support reactive to bind and immobilize a targeted component of said body fluid upon contact with the capture support;
   (c) at least two compartments suitable for the storage of chemical reactants and solutions, including:
      (i) at least one compartment containing a reagent that is reactive with said targeted component to modify said targeted component; and
      (ii) at least one compartment containing a reagent that causes release of said targeted component from said capture support,
   wherein said compartments are connected to said sequestering chamber;
   (d) conduits and/or channels connecting said compartments to said sequestering chamber, said connections further comprising valves for regulating the flow of fluid between said compartments and said sequestering chamber;
   (e) pumping means for driving fluid flow through said apparatus;
   (f) an outlet configured to access the body fluid circulatory system of said mammalian subject and introducing body fluid exiting said sequestering chamber into said subject;
   wherein said inlet, sequestering chamber, and outlet are connected to provide a closed circuit, and to permit a targeted component modified in said sequestering chamber to be conducted from said sequestering chamber to said outlet.

2. The apparatus of claim 1, further including a partitioning chamber, said partitioning chamber comprised of a filtering means which allows passage of a targeted component of said body fluid to produce a filtrate while retaining other components of said body fluid, and wherein said sequestering chamber is connected to said partitioning chamber so as only to receive filtrate;
   wherein said inlet, sequestering chamber, compartments, conduits and/or channels, and outlet are connected to said partitioning chamber to provide a closed circuit.

3. The apparatus of claim 2, wherein said sequestering chamber comprises an inlet line connected to said partitioning chamber so as to receive fluid flow from the filtrate side of said filtering means and further comprises an outlet line connected to said partitioning chamber so as to conduct fluid flow from said sequestering chamber to the filtrate side of said partitioning chamber.

4. The apparatus of claim 3, wherein the inlet line and the outlet line comprise valves whereby fluid flow between said partitioning chamber and said sequestering chamber may be regulated or stopped.

5. The apparatus of claim 1, wherein said pumping means is capable of driving fluid flow in the direction of the outlet or alternatively in the direction of the inlet.

6. The apparatus of claim 1, wherein said one or more pumping means is a syringe pump, peristaltic pump, piston pump, diaphragm pump, or combination thereof.

7. The apparatus according to claim 2, wherein said filtering means is selected from hollow fiber membranes, flat sheet membranes, membrane cassettes, and rolled sheet membranes.

8. The apparatus according to claim 7, wherein the porosity of said filtering means is from 3 kDa to 50 microns.

9. The apparatus according to claim 7, wherein said filtering means has a pore diameter of from 0.05 to 1 μm.

10. The apparatus according to claim 9, wherein said filtering means has a pore diameter of from 0.05 to 0.2 μm.

11. The apparatus of claim 2, wherein the partitioning chamber is a centrifugal separator.

12. The apparatus of claim 2, further comprising a safety valve to isolate said sequestering chamber and/or said partitioning chamber from the fluid source.

13. The apparatus of claim 1, wherein said closed circuit is sterile or sterilizable.

14. The apparatus of claim 1, wherein the capture support comprises a matrix material which is either porous or nonporous.

15. The apparatus of claim 1, further comprising one or more additional sequestering chambers having capture supports of the same or different composition and functionality.

16. The apparatus of claim 15, wherein said plurality of sequestering chambers provide a multistage separation circuit capable of binding or reacting with several different targeted components.

17. The apparatus of claim 1, wherein the capture support binds the targeted component.

18. The apparatus of claim 1, wherein the capture support is capable of binding or reacting to more than one targeted component.

19. The apparatus of claim 1, wherein the targeted component is a complex, assembly, or cell.

20. The apparatus of claim 1, further comprising a port or outlet which allows the sampling or removal of all or part of the targeted component, either before or after modification, without compromising the closed system.

21. The apparatus of claim 1, wherein a plurality of in-line filters of the same or different functionality are disposed between any of the compartments and the chamber or chambers they are connected to.

22. The apparatus of claim 1, wherein the sequestering chamber is suitable for performing modification of the targeted component by covalent or non-covalent binding of a functional moiety to the target component.

23. The apparatus of claim 22, wherein the modification is by the chemical or physical alteration of the target component.

24. The apparatus of claim 1, further comprising a port for introduction of a modifying reagent into the sequestering chamber without compromising the closed system.

25. The apparatus according to claim 1, wherein said capture support comprises a solid support having antibodies, antibody fragments, binding peptides, or aptamers immobilized thereon.

26. The apparatus according to claim 25, wherein said capture support comprises Protein A or Protein G.

27. The apparatus according to claim 1, wherein said body fluid is whole blood.

28. The apparatus according to claim 1, further comprising a conduit connecting said inlet and said outlet, said conduit further comprising a safety valve for directing said withdrawn body fluid directly back to said mammalian subject without contacting said sequestering chamber.

29. A closed diversion circuit apparatus comprising:
(a) an inlet configured to access a fluid medium in a bioreactor;
(b) a sequestering chamber connected to said inlet which allows passage of said fluid medium into said sequestering chamber, said sequestering chamber comprising a capture support reactive to bind and immobilize a targeted component of said fluid medium upon contact with the capture support;
(c) at least two compartments suitable for the storage of chemical reactants and solutions, including:
(i) at least one compartment containing a reagent that is reactive with said targeted component to modify said targeted component; and
(ii) at least one compartment containing a reagent that causes release of said targeted component from said capture support,
wherein said compartments are connected to said sequestering chamber;
(d) conduits and/or channels connecting said compartments to said sequestering chamber, said connections further comprising valves for regulating the flow of fluid between said one or more compartments and said sequestering chamber;
(e) pumping means for driving fluid flow through said apparatus;
(f) an outlet configured to access the bioreactor and introducing bioreactor fluid exiting said sequestering chamber into said bioreactor;
wherein said inlet, sequestering chamber, and outlet are connected to provide a closed circuit and to permit a targeted component modified in said sequestering chamber to be conducted from said sequestering chamber to said outlet.

30. The apparatus of claim 29, further including a partitioning chamber, said partitioning chamber comprising a filtering means which allows passage of a targeted component of said fluid medium to produce a filtrate while retaining other components of said fluid medium, and wherein said sequestering chamber is connected to said partitioning chamber so as only to receive filtrate;
wherein said inlet, sequestering chamber, compartments, conduits and/or channels and outlet are connected to said partitioning chamber to provide a closed circuit.

* * * * *